United States Patent [19]

Preziosi et al.

[11] Patent Number: 4,789,637

[45] Date of Patent: * Dec. 6, 1988

[54] ACID COMPLEXED ACETYLENIC COMPOUNDS USEFUL AS ENVIRONMENTAL INDICATING MATERIALS

[75] Inventors: Anthony F. Preziosi, Ledgewood; Thaddeus Prusik, Roosevelt, both of N.J.

[73] Assignee: LifeLines Technology, Inc., Morris Plains, N.J.

[*] Notice: The portion of the term of this patent subsequent to Nov. 29, 2005 has been disclaimed.

[21] Appl. No.: 912,713

[22] Filed: Sep. 29, 1986

[51] Int. Cl.$^4$ .................. G01N 31/22; G01K 11/14; C07C 127/15

[52] U.S. Cl. .................. 436/2; 116/206; 116/207; 116/217; 252/408.1; 260/96.5 R; 422/56; 422/57; 422/58

[58] Field of Search .................. 422/56–58; 436/2; 252/408.1; 116/206, 207, 217; 260/96.5 R

[56] References Cited

U.S. PATENT DOCUMENTS

| | | |
|---|---|---|
| 3,501,303 | 3/1970 | Foltz et al. |
| 3,743,505 | 7/1973 | Bloom et al. |
| 3,999,946 | 12/1976 | Patel et al. |
| 4,125,534 | 11/1978 | Yee |
| 4,189,399 | 2/1980 | Patel |
| 4,208,186 | 6/1980 | Patel .................. 422/56 X |
| 4,208,501 | 6/1980 | Yee et al. |
| 4,215,208 | 7/1980 | Yee et al. |
| 4,235,108 | 11/1980 | Patel |
| 4,238,352 | 12/1980 | Patel |
| 4,276,190 | 6/1981 | Patel |
| 4,278,561 | 7/1981 | Yee .................. 422/56 X |
| 4,373,032 | 2/1983 | Preziosi et al. |
| 4,389,217 | 6/1983 | Baughman et al. .................. 436/2 |
| 4,439,346 | 3/1984 | Patel et al. |

OTHER PUBLICATIONS

G. Wegner, "Topochemical Polymerization of Monomers With Conjugated Triple Bonds"–Die Makromolekulare Chemie 154 (1972) 35–48.

*Primary Examiner*—Barry S. Richman
*Assistant Examiner*—Jill Johnston
*Attorney, Agent, or Firm*—Arthur J. Plantamura

[57] ABSTRACT

A family of acetylenic complexes especially useful as environmental indicators is provided. The complexes include at least one complexing acid and one acetylenic compound of the formula:

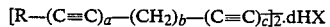

$$[R-(C\equiv C)_a-(CH_2)_b-(C\equiv C)_c]_2 \cdot dHX$$

wherein, a is 1 or 2; b is about 0–5; c is 0 or 1; d is above 0 to about 2, with the proviso that when a is 1, b and c are 0, and when a is 2, b is about 0–5 and c is 0 or 1; and R is —(CH$_2$)n—NHC(O)NHR′; wherein n is an integer of about 1 to 10; and R′ is selected from a group consisting of hydrogen, cycloalkyl, alkenyl, cycloalkenyl, aklyl, phenyl, alkoxyl, alkoxylcarbonylalkyl, and X is a complexing acid.

20 Claims, No Drawings

ACID COMPLEXED ACETYLENIC COMPOUNDS USEFUL AS ENVIRONMENTAL INDICATING MATERIALS

FIELD OF THE INVENTION

An aspect of this invention relates to a novel class of acetylenic complexes comprising a combination acetylenic compound and complexing acid; said complexes are capable of undergoing one or more color changes when exposed to environmental stimuli, and thus useful as environmental indicating materials. Another aspect of this invention relates to environmental indicating devices comprising such complexes, and to the methods of using such devices and complexes to determine environmental changes.

BACKGROUND OF THE INVENTION

As is typical with acetylenic compounds, the acetylenic complexes of the invention change color in response to environmental stimuli due to polymerization via 1,4-addition reactions involving the acetylenic moieties, upon exposure to such environmental stimuli.

Acetylenic compounds that undergo color changes in response to some stimulii are known to the art. For example, acetylenic compounds having at least one —C≡C—C≡C—, have been disclosed as time-temperature history indicators in U.S. Pat. No. 3,999,946 (Patel et al.). Patel et al. discloses monomeric acetylenic compounds of the formula, R—C≡C—C≡C—R, where R includes an alkyl, aryl, benzoate, sulfonate, urethane, acid or alcohol moiety. The compounds disclosed by Patel et al. are colorless and are polymerizable in the solid state, either thermally or by actinic radiation. As the polymerization proceeds, these compounds undergo a contrasting color change to blue or red, and in some instances the color intensifies with time until the compounds finally develop into metallic-looking polymers. Thus, the compounds can be used as time-temperature history indicators and as radiation-dosage indicators. The reference also described polymers of the type [C≡C—CH$_2$)$_m$OCONH(CH$_2$)$_6$NHOCO(CH$_2$)$_m$—C≡C]$_n$ where m is 2, 3 or 4 and n is large, wherein a polymer containing polymeric repeating units of the same empirical formula, undergoes color changes upon thermal annealing.

Other exemplary U.S. patents relating to acetylenic compounds and their use as environmental indicating materials include U.S. Pat. Nos. 4,215,208 (thermochromic materials), 4,125,534 (carbazolyl diacetylenes), and 4,189,399 (co-crystallized compositions).

G. Wegner in an article entitled "Topochemical Polymerization of Monomers with Conjugated Triple Bonds" in Die Makromolekulare Chemie 154, pp. 35–48 (1972) discloses acetylenic compounds having at least one —C≡C—C≡C— moiety and two urea moieties, the urea moieties being separated from the diacetylene by a phenylene moiety. However, the compounds disclosed by Wegner were not very reactive and did not exhibit color changes that would be useful in monitoring environmental exposure.

None of the publications disclose or suggest complexation of acetylenic compounds to produce acetylenic complexes whose reactivity to environmental stimuli is amenable to control. Acetylenic compounds in the art usually display reactivity immediately after synthesis, thus requiring special handling during processing and shipping of articles fabricated from them. Certain of the complexes of the present invention provide a solution to this problem, as complexation provides an alteration in the reactivity of the acetylenic compounds contained in the complexes, even to the extent of complete inactivity. Reactivity is then reinstated at the desired time point by contact with an appropriate reactivating agent.

In other embodiments of the present invention, the reactivity of acetylenic compounds to stimuli is enhanced upon complexation. In further embodiments of the present invention, complexes react spontaneously with moisture, undergoing a readily perceptible color change, thus making them quite useful in moisture indicators.

BRIEF DESCRIPTION OF THE INVENTION

This invention relates to an acetylenic complex comprising at least one complexing acid and at least one acetylenic compound of the general formula:

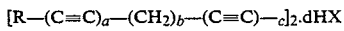

Wherein:
a is 1 or 2, b is about 0–5, c is 0 or 1, d is above about 0 to about 2; with the proviso that when a is 1, b and c are 0, and when a is 2, b is about 0–5 and c is 0 or 1; and R is —(CH$_2$)$_n$—NHC(O)NHR'

Wherein
(1) n is an integer of about 1 to 10; and
(2) R' is selected from the group consisting of:
  (a) hydrogen;
  (b) cycloalkyl;
  (c) alkenyl;
  (d) cycloalkenyl;
  (e) alkyl;
  (f) phenyl;
  (g) alkoxyl;
  (h) alkoxylalkyl;
  (i) alkoxylcarbonylalkyl;

and X is an effective complexing acid.

The present invention also provides a method whereby the activity of acetylenic compounds to environmental stimuli may be altered or controlled by contacting the compound with an effective complexing acid to produce an acid derivative of the compound. Further provided are environmental indicating devices comprising the acetylenic complexes of the invention, and methods using such devices to assess environmental changes.

DETAILED DESCRIPTION OF THE INVENTION

This invention relates to novel acetylenic complexes that are particularly useful for monitoring the environmental exposure of an item. This could take the form of monitoring various products that undergo progressive quality changes upon exposure to environmental stimuli. Environmental stimuli includes such stimuli as temperature, cumulative time-temperature, moisture, pressure, and radiation exposure.

An "effective complexing acid" in the present invention is one that is capable of altering the reactivity of the acetylenic compounds in response to stimuli so that the reactivity of the complex to stimuli differs from that of the acetylenic compound in the absence of complexation. This alteration may take many forms, including but not limited to, enhancing the activity of the acetylenic compounds in response to various stimuli, and achieving activity in response to stimuli with compounds previously inactive to such stimuli. Other alterations include reversibly inactivating compounds previously active to stimuli. These complexes may then be reactivated prior to exposure to such stimuli. And yet another modification is the alteration of acetylenic compounds by complexing, resulting in a complex capable of spontaneously reacting with moisture, as evidenced by a color change.

The effective complexing acids of the present invention vary widely and may be chosen from those that will form an "adduct" with the di-urea moities of the acetylenic compound. As used herein an "adduct" is a chemical addition product. In this regard, it is believed that the complexing acid protonates one or more of the urea functions of the acetylenic compound forming a positively charged species which then associates ionically with the counter anion of the acid. Further, while the present inventors do not wish to be bound by any theory, it is believed that this complexation exerts control over the activity of the original acetylenic compound by re-orienting its urea side-chains, which in turn has the effect of altering the 1,4-additon reaction of the acetylenic molecules that would normally result in a color change upon exposure to environmental stimuli. This re-orientation results in a new color reactivity, or an enhancement, reduction or complete suspension of an existing color reactivity to environmental stimuli.

Particularly suitable acids to accomplish this complexing may be selected from the halo-acids, illustrative of which are the hydro-halo acids HCl, HBr, HF, HI, and HA. Preferred among the hydro-halo acids are HCl, HF, HBr, and HI. Particularly preferred are HCl and HBr. For the most part, these acids may be readily obtained commercially.

The properties of the acetylenic complexes of the present invention and their preparation are discussed in more detail herein below following the description of preferred urea acetylenic compounds in the complexes, and methods for their syntheses.

Acetytenic compounds for use in the practice of the invention are those of the general formula:

$$[R-(C\equiv C)_a-(CH_2)_b-(C\equiv C)_c-]_2$$

Wherein:
a is 1 or 2, b is about 0–5, c is 0 or 1; with the proviso that when a is 1, b and c are 0, and when a is 2, b is about 0–5 and c is 0 or 1; and R is $-(CH_2)_n-NHC(O)NHR'$ Wherein:
(1) n is an integer of about 1 to 10; and
(2) R' is selected from the group consisting of:
 (a) hydrogen;
 (b) cycloalkyl;
 (c) alkenyl;
 (d) cycloalkenyl;
 (e) alkyl;
 (f) phenyl;
 (g) alkoxyl;
 (h) alkoxylalkyl; and
 (i) alkoxylcarbonylalkyl.

The preferred acetylenic compounds in the complexes of this invention are of the general structures I, II, and III as depicted hereinbelow Structure I represents the most preferred family of compounds and is as follows:

$$[R'-NH-\overset{O}{\underset{\|}{C}}-NH-(CH_2)_n-C\equiv C-]_2$$

wherein n is an integer from about 1–10; R' is an organic moiety comprising one or more moieties selected from the group comprising a cycloalkyl moiety from about 3–7 carbon atoms, an alkenyl moiety from about 3–18 carbon atoms, a cycloalkenyl moiety from about 3–7 carbon atoms, an alkoxy moiety from about 2–18 carbon atoms, a linear or branched alkyl moiety from about 1 to 18 carbon atoms, an alkoxycarbonylmethylene moiety from about 3–14 carbon atoms, or a phenyl moiety.

In many preferred embodiments of the invention in which acetylenic compounds of Structure I are used, R' is a linear or branched alkyl moiety from about 1–18 carbon atoms, an alkoxycarbonylmethylene moiety from about 3–13 carbon atoms, or a phenyl moiety. The linear alkyl moieties are especially preferred. Especially preferred alkyl moieties include ethyl, n-propyl, n-butyl, n-hexyl, n-octyl, n-dodecyl and n-octadecyl. Especially preferred alkoxycarbonylmethylene moieties include ethoxycarbonylmethylene and butoxycarbonylmethylene. With respect to all compounds of Structure I, n is preferably about 1–4 and more preferably about 1.

Other preferred acetylenic compounds of this invention include the split tetraynes and hexaynes. The split tetraynes and hexaynes are illustrated by general Structures II and III as follows:

$$[R'-NH-\overset{O}{\underset{\|}{C}}-NH-(CH_2)_{\overline{n}}-C\equiv C-C\equiv C-(CH_2)_b]_2 \quad \text{II}$$

$$[R'-NH-\overset{O}{\underset{\|}{C}}-NH-(CH_2)_{\overline{n}}-C\equiv C-C\equiv C-(CH_2)_{\overline{b}}-C\equiv C]_{\overline{2}}$$

wherein R' is as described for Structure I; n is an integer from about 1 to 4; and b is an integer of about 1 to 6.

Syntheses of the acetylenic compounds used in the novel complexes of this invention may be easily accomplished by employing procedures which are well known by those having skill in the art of organic chemistry. For example, in the acetylenic compounds of general Structure I wherein n is about 1, the most preferred group of compounds for complexation may be synthesized by the following two step reaction scheme:

$$H_2NCH_2-C\equiv CH + R'-N=C=O \xrightarrow{THF}$$

$$R'NH\overset{O}{\underset{\|}{C}}NHCH_2-C\equiv CH \xrightarrow[O_2]{CuCl/N,N,N',N'-\text{tetra-methylethylenediamine}}$$

$$[R'NH\overset{O}{\underset{\|}{C}}NHCH_2-C\equiv C-]_2$$

wherein R' is as described hereinabove. In the above synthetic route, monopropargylamine is reacted with a suitable isocyanate (i.e., having the desired R' group conforming to the R' groups as described for compounds of general Structure I) in the presence of tetrahydrofuran or other similar solvents such as 2-methoxyethyl ether to form an alkyne intermediate having a urea moiety and the desired R' group. The first reaction shown above will occur at temperatures between about 25° C. and about 50° C. and requires a reaction time between about 1 and about 2 hours. A catalyst is not required for the reaction. Thereafter, without isolation of the intermediate, the intermediate is oxidatively coupled via conventional procedures to produce the final product. The oxidative coupling reaction may be conducted at temperatures between about 25° C. and about 50° C. and will generally require only about 2 to about 4 hours to complete. Isolation of the product from the reaction mixture may be accomplished by conventional procedures such as precipitation, filtration, recrystallization, and the like.

Syntheses of compounds of general Structure I wherein n is about 2–10 is somewhat more complex, but conventional procedures are also available for production of compounds of this nature. These compounds may be formed by a five step reaction scheme that initially involves oxidatively coupling an acetylenic compound having a terminal hydroxyl moiety such as 3-butyn-1-ol, 4-pentyn-1-ol, 5-hexyn-1-ol or the like to the corresponding diyn-diol. The diyn-diol is then reacted with p-toluenesulfonyl chloride to form a bis(p-toluenesulfonate) compound. This reaction employs tetrahydrofuran or another similar solvent as a reaction medium and pyridine is employed as a promoter. The diyn-bis(p-toluenesulfonate) compounds are then converted to diphthalimido-diyn compounds using a Gabriel type synthesis as described in an article entitled "The Gabriel Synthesis of Primary Amines," *Angew. Chem. Internat Edit.*,7,919 (1968) by M. S. Gibson and R. W. Bradshaw, said article being incorporated herein by reference. Thereafter, the dipthalimido-diyn compounds are hydrolyzed via a two stage hydrolysis to produce a diyn-diamine salt. The two-stage hydrolysis that should preferably be employed is also described in the Gibson and Bradshaw article. Finally, the diyn-diamine may be reacted with a suitable isocyanate, R'—N=C=O, in accordance with the procedures described herein where n is about 4 to produce the di-urea having the desired R' groups with n of about 2–10.

Syntheses of the tetraynes in the complexes of general Structure II and the hexaynes in the complexes of general Structure III is preferably accomplished by the following reaction scheme:

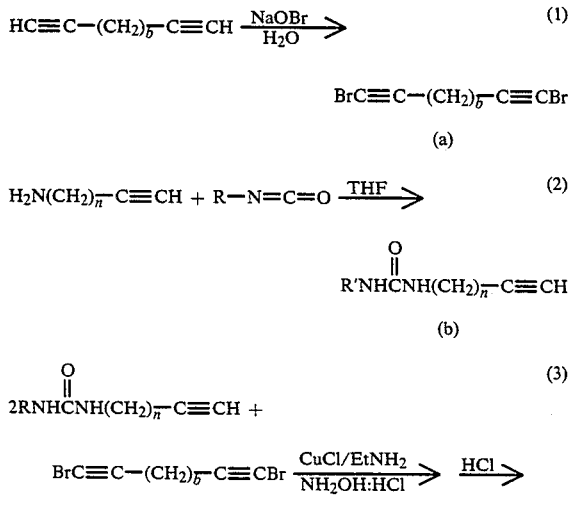

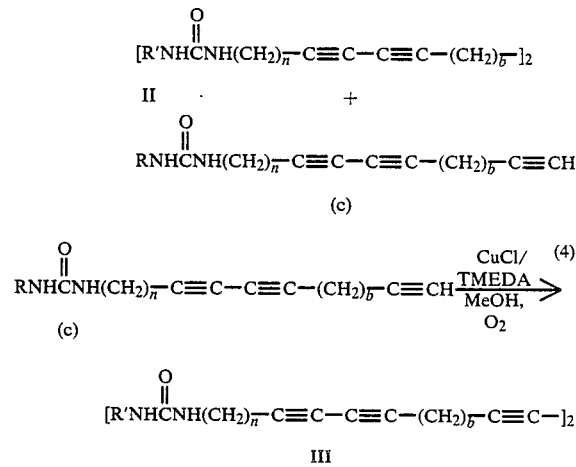

In reaction (1) above a diyne having b of about 1–6 is reacted with a suitable hypobromite such as sodium hypobromite to produce a dibromo diyne compound (a). Reaction (2) involves reacting an alkyne having a terminal primary amine wherein n is about 1–10 with an isocyanate having a suitable R' group as described hereinabove to produce urea (b) having a terminal acetylene moiety and desired R' group. Thereafter, compounds (a) and (b) are coupled using a Cadoit-Chodkowicz reaction technique in the presence of a solution comprising CuCl, n-ethylamine and hydroxylamine hydrochloride to produce tetraynes of general structure II. The triyne (c) in the above reaction scheme may be extracted from the reaction medium by addition of a non-polar solvent such as petroleum ether, heptane, or hexane or the like. Thereafter, triyne (c) may be oxidatively coupled to hexaynes of general Structure III by well known procedures such as the Hay coupling technique in accordance with reaction 4 above.

In general, prior to carrying out the complexing reactions as described hereinbelow, it is preferred to recrystallize the above acetylenic compounds to obtain compound in a pure form and to avoid premature polymerization via the 1,4 addition reaction, which results in undesirable polymer particle formation. Recrystallization may be carried out by conventional dissolution and recrystallization techniques. The compounds are dissolved in a suitable heated solvent such as an organic acid, illustrative of which are acetic acid, propionic acid, butanoic acid, and the like; alcohols, ethoxyethanols, 2,6-lutidine, chlorobenzene, pyridine, and the like. To avoid a premature 1,4 addition reaction, it is preferable that the chosen solvent be heated to approximately 15° C. to about 20° C. below its boiling point. The solvated compounds are then recrystallized by cooling at a moderate rate to about 15° C. to about 20° C. by use of a cold water bath or the like.

The complexes of the present invention are obtained by treatment of the acelytenic compounds with the various effective acid complexing acids, said treatment effectuated by simply mixing the two components together when in a liquid phase, or vapor exposure of the acid to the acetylenic compound. Reaction schemes producing the preferred complexes of the invention include:

Scheme 1

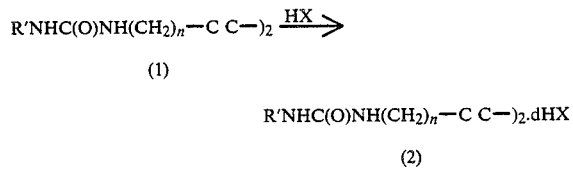

where n = 1 and 4; d = about 0-2; X = F, Cl, Br, and I; R' = alkyl and aromatic

Scheme 2

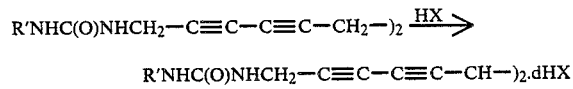

where X = Cl and Br; R' = alkyl

Scheme 3

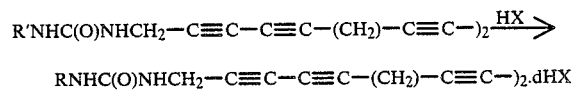

Where X = Cl and Br; R' = alkyl

The preferred methods of obtaining the complexes of the present invention include vapor exposure of the complexing acid to the conjugated acetylenic derivative as well as direct contact, such as with a concentrated acid. An effective amount of the acid complexing agent is an amount that will complex the acetylenic compound to any extent. Thus, the amount of acid used is not critical and is often in excess of that needed for the complexing to take place. The acid may be in pure form or contain other components that do not interfere with the complexation. For example, the complexing may be in the presence of a metal salt, especially a Group II metal salt.

Direct contact with the acid complexing agent in a liquid form may generally be accomplished by contacting the acetylenic urea compound with a quantity of the liquid acid sufficient to cover the surface thereof. Heat may then optionally be applied in the range of about 40° C.-100° C. with about 60° C.-75° C. preferred.

The resulting complexed compound is then removed from this acid bath and cooled if need be. The compound is then preferably filtered and washed with a suitable solvent or succession of solvents to remove excess complexing acid. Particularly useful solvents for this purpose are non-hydrolytic solvents such as THF, ether, xylenes, heptane, acetone, and the like, because these will not decomplex the adduct. In a particularly preferred embodiment, the complexed compound is washed with a xylene, followed by heptane.

Vapor exposure may be accomplished by suspending the acetylenic compound over a concentrated commercial acid solution for a time sufficient to perceive wetting of the substrate, preferably about 30 seconds to about 3 minutes, most preferably about 1 minute to about 2 minutes. Adequate complexation may be evidenced by a slightly wet appearance.

When in the active form, the complexes of this invention undergo incremental or progressive color changes upon exposure to environmental stimuli. Thus, there is a corresponding change in reflectance or reflectivity due to exposure to environmental stimuli. Reflectance or reflectivity is defined as the amount of light at selected wavelengths that is reflected by an indicating material after said light has impinged upon the indicating material. A perfectly reflective material has a reflectance or reflectivity equal to one. Percent reflectance or reflectivity is equal to one hundred times the reflectivity. Since the complexes undergo reflectivity changes upon exposure to environmental stimuli, said complexes will undergo contrasting color changes upon exposure to given amounts of actinic radiation or thermal annealing. The term "thermal annealing" refers to heating at sufficient temperatures, as by infrared radiation, flame, heat gun, laser-beam, and the like which is sufficiently high to cause polymerization by 1,4-addition of the acetylenic moieties in the complex.

The complexes of this invention exhibit highly desirable properties which render them an especially preferred class of materials for use as environmental indicating materials in environmental monitoring devices. In their reactive state, many of the complexes of this invention undergo a color change from white, pink, or light gray to various shades of blue upon exposure to environmental stimuli and will thus absorb light in a spectral region ranging from about 250 nm to about 700 nm. Thus, environmental indicator labels prepared from the complexes of this invention may be read by optical scanners consisting of a light source capable of illuminating a surface; a detector to sense the amount of reflected light; and a means to output the signal from the optical detector that operate in this spectral region.

Complexes of this invention containing the alkyl ureas of general Structure I (the most preferred class of compounds) wherein R' is a linear alkyl of about 1-18 carbon atoms are especially useful in this respect, as most ureas of this nature gradually polymerize to a blue color upon being exposed to environmental stimuli, with speed of polymerization and degree of color response being directly related to the amount of environmental exposure, derivative, or recrystallization processes.

The complexes of the invention are also especially useful because they characteristically either melt at high temperatures, generally above about 170° C., or they do not melt at all but simply polymerize rapidly at temperatures above about 175° C., resulting in a dark blue-black color. Thus, heating of the complexes often results in color intensification upon reactivity to environmental stimuli. This is a highly desirable feature in addition to the optimal spectroscopic properties of these complexes, as many of the acetylenic compositions described in the prior art melt at modest temperatures, the melting taking place when the compound is only partially polymerized. It should be appreciated that this melting of a partially polymerized acetylenic composition can cause a color change which could yield false information regarding cumulative temperature exposures.

Superior color responsiveness to environmental stimuli, in particular cumulative time/temperature stimuli, may be preferably achieved with the complexes of the present invention wherein R' of the general acetylenic compound Structures I, II, and III is a linear alkyl moiety of about 1 to 12 carbon atoms; preferably about 2-9 carbon atoms; most preferably about 8 carbon atoms. A particularly preferred complex is obtained with the HCl derivative of the octyl diurea of Structure I, particularly when the acetylenic compound is treated with liquid phase HCl acid and recrystallized to obtain the complex. Table 11 demonstrates that the acetylenic di-urea becomes more color reactive after treatment with HCl acid as evidenced by a rapid change to blue after UV treatment, instead of a more typical orange, red or yellow. Comparison with an untreated sample reveals that the compound responds more quickly both thermally and under UV, typifying color-responsive enhancement.

Color responsiveness to environmental stimuli unattainable prior to complexation may be achieved upon complexation of certain of the compounds. This occurs when R' in the general acetylenic compound Structures I, II, and III is an organic moiety of about 1-5 carbon atoms, preferably about 1-3 carbon atoms, and most preferably the methyl or isopropyl moiety. In a particularly preferred embodiment, the acetylenic compound is the methyl or isopropyl derivative, and the complexing agent is HBr. Tables 3 and 10 which follow demonstrate that acetylenic di-ureas normally non-color active either thermally or under UV light, become color active after acid treatment.

Certain complexes of the present invention demonstrate superior moisture sensitivity. Particularly preferred moisture sensitive complexes may be obtained from complexation of acetylenic compounds of general Structures I, II, and III wherein R' is selected from the group consisting essentially of linear, branched, or cyclic alkyl moieties of about 3-18 carbon atoms, an alkoxy of about 2-18 carbon atoms, or an alkoxycarbonylmethylene moiety of about 3-14 carbon atoms. In particularly preferred embodiments, the derivatives are complexed with HCl or HBr, preferably HBr. The complexes are then activated by thermal or actinic radiation, such as ultraviolet, gamma and the like, to affect 1,4 polymerization. However, this activation and resulting polymerization does not evidence the typical blue color indicative of long chain polymers. The blue color is achieved upon subsequent exposure to moisture, which may have the effect of reorienting the side chains in the polymer molecules to allow the change in color. For example, many of the halo-urea derivatives of the acetylenic di-ureas change to orange, red or yellow after UV treatment. Then the color may change to blue when contacted with water making them potentially useful in moisture indicators. Color responsiveness to water is a property the acetylenic compounds did not demonstrate prior to complexation.

The moisture sensitive complexes of the present invention offer superior sensitivity in the detection of moisture, as liquid or vapor phases of varying kinds and degrees serve to effect a color change. Ambient moisture may be detected, as well as immersion in water or mixtures of water and other components in a liquid phase. Ambient humidity values of above about 40% may readily be detected over a period of hours, with higher humidity values detectable in a matter of minutes. Several factors affect the moisture sensitivity of the complexes, such as the amount and thickness of the surface area of the complexed compound exposed to the moisture, length of time of the exposure, amount of complexing agent present in a layer of compound exposed to moisture, and the like. One of skill in the art should have no difficulty in optimizing these and other such parameters for desired use.

The moisture sensitivity of the complexed compounds may also be controlled by coating a substrate containing the complexed compound in whole or in part with a layer of polymeric material, such as polyvinyl (chloride), poly(ethylene), polybutadiene, cellulose, or polystyrene, and the like. Such a coating serves to alter the rate at which the moisture reaches the complexed compound The thickness of such a protective layer governs in part the degree of control exerted over the reactivity to moisture. Generally speaking, the thicker the layer, the more moisture required for reactivity or the longer the time required for absorption of the moisture to evidence the reactivity.

It is within the contemplation of the present invention to utilize the moisture sensitivity properties of the complexes described above in a moisture indicator system. In accordance with one aspect of the present invention, moisture indicators fabricated with the present complexes would preferably be activated from a UV source and protected from moisture until desired use with a protective moisture strip, impermeable packing or any suitable protective measure. When it is desired to use the indicator, the protective measure is simply removed and the indicator exposed.

A superior active-inactive-activatable system is achieved with certain of the complexes of the present invention. Preferred complexes for this purpose comprise the general acetylenic compounds of Structure I, II, and III, wherein R' is a linear alkyl organic moiety of about 1-5 carbon atoms, preferably about 2 carbon atoms, and a hydro-halo complexing acid. Particularly preferred are the acetylenic compounds of Structure I with 1-3 carbon atoms, especially the ethyl derivative, in conjunction with HCl, in liquid form or vapor phase. In this aspect of the invention, an acetylenic compound is rendered inactive by complexation.

Reactivation of an acetylenic complex whose activity has been thus diminished may be effected by exposing the complex to some stimuli. For example, such reactivation may completely or in part be effected by a hydrolytic process which better coordinates the complexing agent, so that polymerization by 1,4 addition may take place. This hydrolytic process may be accomplished by a variety of means such as contact with a hydrolytic solvent in liquid or vapor form.

Contact with such a hydrolytic solvent may be accomplished with a variety of solvents that regenerate the original non-complexed alkylene. Illustrative of these are water, alcohols, dilute organic acids, dilute inorganic acids and amines. Preferred among these are N,N,N',N'-Tetramethylethylenediamine, glycerol, acetic acid, water, and methanol, any of these alone or in combination.

Contacting the complex with the vapor form of the hydrolytic solvent may be accomplished by conventional methods such as heating or bubbling an inert gas into the solvent source. Useful solvents in the vapor form may be selected from water, alcohols, organic acids, and amines, particularly preferred being water and methanol. Most preferred for purposes of reactivation is water, whether in liquid or vapor phase.

The ethyl derivative in Structure I (Preparation Example A) serves as an illustration of the above process. This compound can be inactivated by HCl vapor or liquid. Reactivation is then easily effected by moisture contact to develop a blue color.

Devices containing the inactive-activatable acetylenic complexes of the present invention are particularly useful as time-temperature indicators, as indicators fabricated from such complexes may be completely inactivated, making processing and shipping possible without the need for temperature control. The indicators may then be reactivated for use at the intended destination by a variety of means as discussed hereinabove.

The acetylenic complexes of this invention may be fabricated into the various environmental indicator devices described herein in accordance with well known procedures. An environmental indicating device is a device that may be attached in some form to an item that undergoes progressive changes in response to environmental exposure, said device being capable of recording the amount of environmental exposure of said item. For example, product quality of a perishable item may be monitored by color changes. These changes are correlated with product quality by color matching procedures when a certain color corresponds to a given amount of product degradation. The acetylenic complexes of this invention record the amount of environmental exposure by color changes that may be determined by visual observation or by an optical scanning method using techniques as described above.

Substrates that may be employed for construction of devices that employ the acetylenic complexes of this invention may vary widely and include paper, paperboard, fiberboard, cardboard, Kimdura, Mylar TM, polyethylene, polypropylene, polyacrylate polymers and copolymers, cellulose ethers, cellulose esters, mixed esters or other similar materials. Exemplary of other materials that may be employed as substrates for environmental indicator labels that employ acetylenic complexes of this invention include synthetic resins and plastics. Additionally, it should be appreciated that containers for various products may also serve as a substrate upon which the environmental indicator labels are constructed.

The complexes of this invention may be applied to the substrate in various fashions. In the fabrication of indicator devices, it is preferred to apply the uncomplexed compound to the substrate and thereafter complex as described above. For example, an ink solution comprising an acetylenic compound and a good solvent (i.e. one that readily dissolves the urea) may be sprayed onto the substrate in order to deposit the acetylenic compound onto the desired area of the substrate. This ink system could also be applied to the substrate by more conventional methods such as flexography, screen, gravure, letter-press, ink-jet printing, or the like.

In general, a solvent with a binder such as lacquer may be employed to dissolve the acetylenic compound The concentration of compound in this solution may vary widely. Usually, the solution should include the acetylenic compound in an amount comprising about 1% to about 5% and preferably about 1% to 2% by weight. This method, in effect, employs an acetylenic compound as a dye (i.e., compound soluble in the ink vehicle). This method is more particularly described in U.S. Pat. No. 4,189,399. Complexation of the uncomplexed compound, now affixed to the substrate, is then effected by exposure to an acid according to the methods of the invention.

Solvents that may be employed for forming the above-described ink solutions include acetic acid, propanoic acid, heptanoic acid, nonanoic acid, hydroxy acetone, 1,1,3,3-tetramethylurea, triethanolamine, n-decylamine, sec-phenethyl alcohol, dimethyl sulfoxide, 2,5-lutidine, and the like, providing these solvents are evaporated from the substrate prior to the complexation procedure.

Another, and more preferred, method for applying the acetylenic complexes of this invention to the indicator device substrates involves initially grinding the acetylenic complex into fine particles and forming a suspension of the particles in a suitable binder-solvent system. Suitable binders for forming these suspensions are those that will not decomplex the acetylenic complexes and include synthetic plastics, resins, waxes, nonacqueous gels, and the like. The suspension comprising the binder and the acetylenic complex may then be applied to the desired area of the substrate by spraying, screen printing, gravure, flexography letterpress, or other conventional printing means.

ACETYLENIC DIUREA COMPOUND PREPARATION EXAMPLES A-R

General Procedure for Preparing Acetylenic Compounds for Use in the Present Invention A three neck flask fitted with a stirrer, thermometer, $N_2$ flow tube which was exchanged with an $O_2$ dip tube for oxidative coupling reactions, and a dropping funnel was employed for producing the compounds of Examples 1–15. An excess of an isocyanate compound dissolved in tetrahydrofuran (hereinafter referred to as THF) was added dropwise to the reaction flask to which a solution comprising mono-propargylamine and THF had been previously added. Since the reactions were rapid, a catalyst was not employed. To moderate the temperature of the reaction, a water bath (typically 18° C.) was used during the addition of the isocyanate. After 1 to 2 hours, the Hay coupling technique was used, whereby the reaction media was charged with CuCl and complexation agent, N,N,N',N'-tetramethylethylenediamine (hereinafter referred to as TMEDA), followed by a continuous moderate bubbling of $O_2$ to effect the oxidative coupling reaction. A water bath was used to moderate the intitial temperature excursion. Typically, after 2½ hours, the medium was deactivated with HCl. Purification was effected by filtration, washings, and recrystallization.

In cases where ultraviolet radiation was employed to cause polymerization and corresponding color changes of the acetylenic ureas, the ultraviolet source employed was a model UVS-11E ultraviolet lamp (Ultra Violet Products Inc., Pasadena, Calif.)

EXAMPLE A 2,4-hexadiyn-1,6-bis(ethylurea)

A 1 liter flask was charged with 50 g (0.9 mol) monopropargylamine and 300 mL THF. 89 g (1.25 mol) ethylisocyanate diluted with 50 mL THF was added dropwise over a 30 minute time period. During the addition, the reaction flask was placed in a water bath (18° C.) to moderate the exotherm during the ethylisocyanate addition. The temperature did not exceed 40° C. 2.5 g CuCl and 6 mL TMEDA were added to the reaction media after 1½ hours. Oxygen was bubbled into the reaction medium at a moderate rate while stirring. Initially, a water bath was used to keep the temperature between 25° to 35° C. The water bath was removed after 15 minutes and the temperature slowly rose to 55° C. and then decreased. After 2½ hours, the medium was deactivated by adding 200 ml/10% HCl solution. The product was filtered, washed with additional HCl solution, followed by washing with $H_2O$.

The product was stirred in a solution of 200 mL methanol and 200 mL 10% HCl solution, filtered, washed with H$_2$O, methanol, and finally acetone. The product was recrystallized by dissolving it in 500 mL hot acetic acid (90° C.), filtering, and cooling to 15°–20° C. The precipitate was filtered, washed with petroleum ether (50°–110° C.) and then vacuum dried for about 1 to 2 hours. Yield: 88 g (78% of theoretical) fine powder product which turned blue at a moderate rate under ambient conditions, about 25° C., in the dark. The product did not melt when heated to 300° C. on a Mettler hot stage. Upon heating, rapid polymerization to dark blue and then black occurred.

ELEMENTAL ANALYSIS $C_{12}H_{18}N_4O_2$(MW=250.277) Calcd. C 57.59; H 7.25; N 22.38; O 12.78; Found. C 57.47; H 7.34; N 22.45; O 12.73.

EXAMPLE B 2,4-hexadiyn-1,6-bis(butylurea)

Same as Example A except 25.8 g (0.25 mol) butylisocyanate diluted with 25 mL THF and 10.0 g (0.18 mol) mono-propargylamine in 100 mL THF was used to synthesize the mono-urea derivative. The complexing agent was derived from 1 g CuCl and 3 mL TMEDA to form the diurea The reaction media was deactivated with 125 mL HCl (10%). The methanol, acetone, and water used in the work-up were reduced proportionally to Example 1. Yield: 26.6 g (97%) of a greenish product which moderately changed to blue at ambient conditions (about 25° C.) in the dark indicating an active phase.

A 1 g sample was recrystallized from 100 mL ethanol. Initially, the color of the recrystallized product was light pink, but the color slowly changed to orange at ambient conditions (about 25° C.). Upon irradiation for 5–10 seconds with the UV source, the color of the product changed to blue. When the product was recrystallized from acetic acid (1 gm/10 ml) instead of ethanol, the orange, phase also occurred. However, when the product was recrystallized from Cellosolve ® (1 gm/18 ml) followed by acetic acid (1 gm/10 ml) only the blue phase occurred. An orange to blue phase transition may be obtained by heating the former product to approximately 65° C.

ELEMENTAL ANALYSIS $C_{16}H_{26}N_4O_2$(MW=306.385) Calcd. C 62.72; H 8.55; N 18.28; O 10.44; Found. C 62.53; H 8.81; N 18.08; O 10.01.

EXAMPLE C 2,4-hexadiyn-1,6-bis(octylurea)

Same as Example A and B except 21.5 g (0.14 mol) octylisocyanante, 6.6 g (0.12 mol) mono-propargylamine, and 200 mL THF were used to synthesize the mono-urea. A proportionally larger amount of THF was necessary to keep the mono-urea solubilized. Synthesis of the mono-urea required 1 hour at 25° C. 1 g CuCl, 3 mL TMEDA, and 50 mL THF were added to the reaction media for the coupling reaction to obtain the di-urea. The temperature was maintained between 45°–50° C. throughout the reaction. The coupling reaction was complete in 2 hours. Yield: 25.2 g (99%) of light blue product which melted and decomposed at about 195° C. upon heating. The product was recrystallized from ethanol (1 g/40 mL) (it may also be recrystallized from acetic acid at the ratio of 1 g/15 ml). The recrystallized product was thermochromic and underwent a light blue to red-purple reversible transition at 80° C.

ELEMENTAL ANALYSIS $C_{24}H_{24}N_4O_2$(MW=418.626) Calcd. C 68.86; H 10.11; N 13.38; O 7.64; Found. C 68.83; H 10.34; N 13.23; O 7.60.

EXAMPLE D 2,4-hexadiyn-1,6-bis(dodecylurea)

Same as Example A and B except 25 g (0.45 mole) monopropargylamine, 100 g (0.47 mole) dodecylisocyanate, 350 mL THF were used to form the mono-urea. After the addition of the isocyanate, the temperature was increased to 45°–50° C. to keep the product solubilized. The reaction was continued for 1 hour at which time 2.5 g CuCl and 6 mL TMEDA were added to the reaction media. The temperature was maintained between 45°–50° C. for 2½ hours; the product precipitated as it formed (the temperature during this reaction should not exceed 50° C. because above 50° C. appreciable polymer formation occurs). The product was deactivated with a 1:1 mixture of 20% HCl solution/MeOH (500 mL), filtered and washed twice with methanol and acetone. The resulting product was yellow. The yellow color intensified upon exposure to ultraviolet light. Upon placing a sample of the product on filter paper and applying mechanical pressure with a spatula to the product, subsequent UV irradiation or thermal annealing changed the yellow color to blue. It was also found that rapidly heating the yellow phase above about 150° C. results in an abrupt color change from yellow to blue-purple. In order to recrystallize the product, it was added to 2.5L dimethylsulfoxide, heated to 80°–85° C. on a hot plate, and rapidly brought up to 95° C. before it was removed and filtered. The product was precipitated with 1.3L ethanol, filtered, and washed with additional ethanol followed by petroleum ether (50°–110° C.). Yield: 112 g (93%) pale to light blue product which melted and decomposed at 215° C. upon heating.

ELEMENTAL ANALYSIS $C_{32}H_{58}N_4O_2$(MW=530.842) Calcd. C 72.40; H 11.01; B 10.55; O 6.03; Found. C 72.25; H 11.13; N 10.65; O 6.10.

EXAMPLE E 2,4-hexadiyn-1,6-bis(octadecylurea)

Same as Examples A and B except 10.6 g (0.036 mol) n-octadecylisocyanate, 2.0 g (0.036 mol) mono-propargylamine, and 75 mL THF were used to snythesize the mono-urea. The reaction proceeded for 1 hour at a temperature between 50° C.–60° C. The coupling reaction was conducted using 0.25 g CuCl and 3 mL TMEDA, allowing the reaction to continue for 2½ hours at 45°–50° C. Yield: 11.8 g (94%) light yellow product which changed to a dark yellow upon exposure to 5–10 seconds of ultraviolet tradiation. A sample (about 0.5 g) was placed on filter paper. Mechanical pressure (i.e., shearing with spatula) was applied to the product. Following the application of pressure, the product was irradiated with ultraviolet radiation and the color of the product changed from yellow to blue.

EXAMPLE F 2-4-hexadiyn-1,6-bis(n-propylurea)

Same as Examples A and B except 2.0 g (0.03 mol) mono-propargylamine, 3.1 g (0.036 mol) n-propylisocyanate, 50 mL THF were employed to synthesize the mono-urea. The synthesis of the mono-urea required 1 hour at 25° C. 0.25 g CuCl and 2 mL TMEDA were added for the coupling reaction which was complete in 2½ hours at 40° C. Yield: 1.7 g (33%) of a yellowish white product which changed to a bright yellow upon exposure UV radiation. Recrystallization from acetic acid (1 g/5 ml) or ethanol (1 g/100 mL) resulted in an active phase in each case which changed from pink to blue upon exposure to UV radiation. Upon heating to 300° C., the product decomposed. A melting point was not observed.

ELEMENTAL ANALYSIS $C_{14}H_{22}N_4O_2$ (MW=278.356) Calcd. C 60.41; H 7.97; N 20.13; O 11.50; Found. C 60.81; H 8.11; N 19.78; O 12.22.

EXAMPLE G 2,4-hexadiyn-1,6-bis(iso-propylurea)

Same as Examples A and B except 2.0 g (0.036 mol) mono-propargylamine, 50 mL THF were used to synthesize the mono-urea and 0.25 g CuCl and 2 mL TMEDA were added for the coupling reaction. Yield: 2.0 g (39%) of a white product which changed to a bright yellow upon exposure to ultraviolet radiation. Recrystallization from various solvents such as acetic acid or ethanol (1 g/170 mL) did not result in an active blue phase when treated with UV light. The product melted and decomposed at 270° C.

ELEMENTAL ANALYSIS $C_{14}H_{22}N_4O_2$ (MW=278.356) Calcd. C 60.41; H 7.97; N 20.13; O 11.50; Found. C 60.84; H 8.09; N 19.75; O 11.93.

EXAMPLE H 2,4-hexadiyn-1,6-bis(methylurea)

Same as Examples A and B except 2.0 g (0.036 mol) mono-propargylamine, 2.1 g (0.036 mol) methylisocyanate, and 50 mL THF were used to synthesize the mono-urea and 0.25 g CuCl and 2 mL TMEDA were added for the coupling reaction. Synthesis of the mono-urea required 1 hour at 25° C. The coupling reaction required 2½ hours at 40° C. Yield: 1.7 g (41%) light pinkish white product which changed to bright yellow upon exposure to 5–10 seconds of ultraviolet radiation. Recrystallization from dimethylsulfoxide, ethanol (1 g/250 mL), or acetic acid did not result in an active blue phase. Upon heating, the product melted and decomposed at 255° C.

ELEMENTAL ANALYSIS $C_{10}H_{14}N_4O_2$ (MW=222.248) Calcd. C 54.02; H 6.35; N 25.21; O 14.40; Found. C 53.96; H 6.60; N 24.48; O 13.32.

EXAMPLE I 2,4-hexadiyn-1,6 bis(ethoxycarbonylmethylene urea)

Same as Examples A and B except 2.0 g (0.036 mol) mono-propargylamine, 4.6 g (0.036 mol) ethylisocyanatoacetate, and 50 mL THF were used for the synthesis of the mono-urea and 0.25 g CuCl and 2 mL TMEDA were added for the coupling reaction. Synthesis of the mono-urea required 1 hour at 25° C. The coupling reaction required 2½ hours at 45° C. Yield: 5.0 g (76%) of a pinkish product which changed to blue upon exposure to 5–10 seconds ultraviolet radiation. Upon heating, the product melted between 190° and 195° C.

ELEMENTAL ANALYSIS $C_{16}H_{22}N_4O_6$ (MW=366.374) Calcd. C 52.45; H 6.05; N 15.29; O 26.20; Found. C 52.13; H 6.05; N 13.01; O 21.61.

EXAMPLE J 2,4-hexadiyn-1,6-bis(butoxycarbonylmethylene urea)

Same as Examples A and B except 2.0 g (0.036 mol) mono-propargylamine, 5.6 g (0.036 mol) butylisocyanatoacetate, and 50 mL THF were used for the synthesis of the mono-urea and 0.25 g CuCl and 2 mL TMEDA were used for the coupling reaction. Synthesis of the mono-urea required 1 hour at 25° C. The coupling reaction required 1½ hours at 45° C. Yield: 3.9 g (51%) of a white product was obtained by recrystallization of the product from ethanol (1 g/75 mL).

A sample of the product turned blue upon exposure to 5–10 seconds of ultraviolet radiation. Upon heating, a sample of the product melted at 168°–169° C. and turned red upon cooling and solidification. The cooled and solidified product turned blue upon exposure to 5–10 seconds of ultraviolet radiation.

ELEMENTAL ANALYSIS $C_{16}H_{22}N_4O_6$ (MW=422.482) Calcd. C 56.86; H 7.16; N 13.26; O 22.72; Found C 57.07; H 7.67; N 13.01; O 21.61.

EXAMPLE K 2,4-hexadiyn-1,6-bis(phenylurea)

Same as Examples A and B except 5.5 g (0.1 mole, 6.2 mL) monopropargylamine, 14.9 g (0.125 mole) phenylisocyanate, and 100 mL THF were used to synthesize the mono-urea and 0.25 g CuCl and 2 g TMEDA were used for the coupling reaction. Synthesis of the mono-urea required 1½ hours at 25° C. The coupling reaction was complete in 2½ hours at 35° C. Yield: 10.5 g (61%) of a white product. Upon expssure to ultraviolet radiation for 1–2 minutes the product underwent a color change from white to light blue. Upon heating to 275° C. the product melted and decomposed.

EXAMPLE L

Synthesis of 2,4,8,10-dodecyltetrayn-1,12,-bis(ethylurea)

This compound was produced by a 3 step synthesis that involved preparing two reactants, 1,6-dibromo-1,5-hexadiyne and 1-propyn-3-ethylurea, and then oxidatively coupling the two reactants.

1,6-dibromo-1,5-hexadiyne was prepared in the following manner:

Sodium hypobromite, NaOBr, was prepared by incrementally adding 120 g (0.732 mole, 39.0 mL) bromine to a 6.35N NaOH solution composed of 76.2 g (1.95 mole) NaOH in 300 mL aqueous cooled to 0° C. The solution was stirred for approximately ½ hours. The solution was added dropwise over a 30 minute period to 1,5-hexadiyne 23.4 g (0.30 mole) and 100 mL $H_2O$ contained in a 1 liter 3-necked flask which was fitted with a mechanical stirrer, thermometer, $N_2$ flow tube to blanket the reactants, and an ice-bath. The temperature was kept below 18° C. throughout the additions. After 3 hours, the solid product was extracted with 100 mL diethylether, washed with $H_2O$ and then kept over 25 g ammonium chloride until needed.

1-propyn-3-ethylurea was prepared in the following manner: To a 500 mL flask fitted with a stirrer, thermometer, $N_2$ flow tube, and a dropping funnel, 75 mL THF and 5.5 g (0.1 mole, 6.9 mL) monopropargylamine was added followed by the dropwise addition of 7.1 g (0.1 mole) ethylisocyanate in 10 mL THF; the temperature was initially moderated with a water bath and continued for 1 hour at room temperature.

In order to oxidatively couple 1,6-dibromo-1,5-hexadiyne and 1-propyn-3-ethylurea to thereby produce 2,4,8,10-dodecyltetrayn-1,12-bis(ethylurea), the Cadoit-Chodkowicz technique was used, whereby, 0.2 g CuCl, 15 mL n-ethylamine (70%) followed by 1.5 g $NH_2OH.HCl$ was added to the reaction media containing the urea. 13.5 g (0.058 mole) 1,6-dibromo-1,5-hexadiyne in 25 mL THF was then added dropwise to the reaction media over a 20 minute period. Initially, the reaction media was cooled with a cold water bath so that the temperature did not exceed 40° C. during the addition. Thereafter, the bath was removed and the reaction was continued with stirring for 2½ hours at a temperature of 25° C. Product precipitation occurred during the addition of the dibromohexadiyne. The product was filtered and washed with several small portions of THF (50 mL 10 total). The filtrate was saved, then the product in the filter funnel was washed twice with a 10% HCl solution, followed by $H_2O$ washings and finally washing with methanol and dried. Yield: 12.1 g (74.2%) pale blue product which changed to dark blue upon exposure to 5–10 seconds ultraviolet radiation. Upon continued irradiation (i.e, 4 minutes), the product changed to a metallic gold color. The product did not melt when heated to 300° C. When heated beyond 300° C., it changed to red, then black, then decomposed.

ELEMENTAL ANALYSIS $C_{18}H_{22}N_4O_2$ (326.40) Calcd C, 66.23; H, 6.79; N, 17.17; O 9.80; Found C, 65.99; H, 6.95; N, 16.88; O 9.77.

EXAMPLE M

Synthesis of 1,5,7-nonatriyn-9-ethylurea

Following the procedure of Example L, the methyl and dodecyl derivatives were prepared. The above compound, a triyne, was recovered from the filtrate of the oxidative coupling reaction of Example L. Addition of petroleum ether (50°–110° C.) to the filtrate caused precipitation of a brown product which was washed with 10% HCl followed by $H_2O$. The product was recrystallized from acetone/petroleum ether (50°–110° C.). Yield: 3.5 g (34.5%) of a white product which changed to red upon exposure to 5–10 seconds of ultra violet radiation.

ELEMENTAL ANALYSIS $C_{12}H_{14}N_2O$ (202.257) Calcd C 71.26; H 6.98; N 13.85; O 7.91; Found C 69.70; H 7.08; N 13.84; O 7.67; Br 1.7. Elemental analysis indicates that 6% of the total theoretically possible bromide remained unhydrolysed.

EXAMPLE N

Synthesis of 2,4,8,10,14,16-Octadecylhexayn-1,18-bis(ethylurea)

This compound was obtained by oxidatively coupling the triyne of Example M. Using the method described in Example A, 1.0 g (0.005 mol) 1,5,7-nonatriyn-9-ethylurea was coupled in a complex composed of 0.25 g CuCl, 2.5 mL TMEDA, and 75 mL methanol, with oxygen being bubbled into reaction media at a moderate rate. The temperature of the reaction media was raised to 60° C. during the initial 5–10 minutes of the reaction time and then heating was discontinued. After 1 hour, 75 mL water was then added. Thereafter, the reaction media was filtered to recover the product. The product was washed with water, $HCl/H_2O$ and then water. The product was recrystallized from 125 mL acetic acid. Yield: 0.5 g (50%) of a light pink product which changed to a blue color upon being irradiated with UV light for 5–10 seconds. After 30 seconds of irradiation, the product changed to a blue-black color.

ELEMENTAL ANALYSIS $C_{24}H_{26}N_4O_2$ (MW 402.5) Calcd. C 71.62; H 6.51; N 13.92; O 7.95; Found. C 70.98; H 6.79; N 13.64; O 8.60. Following the procedures of Examples L, M, and N, the methyl and dodecyl derivatives were also synthesized

EXAMPLE O

Synthesis of 5,7-dodecadiyn-1,12-bis(ethylurea)

This compound was synthesized via the following 5 step reaction sequence:

(a) oxidatively coupling 5-hexyn-1-ol to produce 5,7-dodecadiyn-1,12 diol;

(b) reacting the product of (a) with p-toluenesulfonylchloride to produce 5-7-dodecadiyn-1,12-bis(p-toluenesulfonate);

(c) reacting the product of (b) with potassium phthalimide to produce 1,12-diphthalimodo-5,7-dodecadiyne;

(d) subjecting the product of (c) of a two stage hydrolysis (i.e., base hydrolysis followed by acid hydrolysis) followed by treatment with a base to produce 5-7-dodecadiyn-1,12-diamine;

(e) reacting the product of (d) with ethylisocyanate to produce 5,7-dodecadiyn-1,12-bis(ethylurea).

Reaction steps a–e were conducted as follows:

(a) A 1 liter 3-necked flask was charged with 150 mL methanol, 15 mL TMEDA, and 9 g CuCl. 150 mL 5-hexyn-1-ol was oxidatively coupled using the Hay method by adding it dropwise to the reaction media over a 45 minute time period while oxygen was being bubbled into the reaction media. During the addition, the temperature of the media rose to approximately 60° C., then subsided. Oxygen was bubbled into the reaction media for an additional 15 hours before isolation of the product. Isolation: 800 mL chilled water was added to precipitate the product. The product was filtered and washed with additional water. Recrystallization: The product was dissolved in 100 mL methanol and 5 to 10 mL TMEDA. Precipitation was effected by adding chilled water (8°–11° C.). After filtration and washing with water, the product was recrystallized, again. After removal of most of the water, the product was washed with heptane three times and dried under vacuum. Yield: 120 g of a fluffy white product.

(b) 150 mL pyridine was added dropwise to a solution composed of 58.2 g (0.3 mole) 5,7-dodecadiyn-1,12-diol, (produced from reaction step (a)), 150 g (0.78 mole) p-toluenesulfonylchloride, and 150 mL THF over a 0.5 hour period at a temperature of 20° to 25° C. The reaction was continued with stirring for 6.5 hours at a temperature of 25°–30° C. Isolation: The product was obtained by pouring the reaction media into 1 liter chilled water followed by filtration and several water washings. Recrystallization: The particulate was dissolved in 1.5 liters methanol and refrigerated at −8° C. Thereafter, it was filtered, washed with petroleum ether (50°–110° C.), and vacuum dried. Yield: 110 g (73%) of a light tan product which changed to red upon exposure to 5–10 seconds of ultraviolet radiation. The product had a melting range of 58.5°–59.8° C.

(c) 32.0 g (0.064 mole) 5,7-dodecadiyn-1,12-bis(p-toluenesulfonate) from reaction step (b) and 32.0 g (0.17 mole) potassium phthalimide were reacted in dimethylsulfoxide at 123°–128° C. for 0.5 hours. The reaction media was cooled to 75° C. and 250 mL water was added to precipitate the product. The product was filtered, washed several times with boiling water, acetone, and then heptane. Yield: 24.6 g (85%) of a light tan fine powdered product.

(d) 10 g (0.022 mole) 1,12-diphthalimido-5,7-dodecadiyne, from reaction step (c), 50 mL $H_2O$, 3.1 g (0.055 mole) KOH, 5 mL pyridine and 80 mL ethanol were refluxed for 1 hour then cooled to 50° C.

(e) 30 mL 10N HCl (0.3 mole) was added incrementally to the reaction media followed by 1 g $ZnCl_2$ and refluxed for 3 hours. During the refluxing a product began precipitating (probably the phthalic acid). Isolation: Thereafter, the solvent was reduced by 75%. 100 mL $H_2O$ was added to the reaction media, boiled, filtered, and washed with 50 mL additional boiling $H_2O$. (The filtrant contained 2.5 g (33% of theoretical) phthalic acid; the filtrate contained the diamine-acid salt, $(ClH_3NCH_2-C\equiv C-)_2$, and was observed as two phase separated layers both of which contain the diamine-acid. If the solvent is evaporated from the dark brown layer, a solid forms which changes to blue slowly. The addition of water transforms the blue solid to red). 50 mL 5N NaOH (10 g, 0.25 mole) was added incrementally to the filtrate to neutralize the diamine-acid and generate the diamine. After cooling to 30° C., the diamine was extracted with diethylether (150 mL) by shaking. The ether was distilled leaving 2.5 g yellow semi-viscous crude product.

(f) To the crude product of step (e), 50 mL THF and 3 g of $MgSO_4$ (anhydrous) were added. The solution was filtered and 3.2 g (0.045 mole) ethylisocyanate was added in one-shot at room temperature (25° C.). Heptane was added to fully precipitate the product. It was filtered and washed with additional heptane. Yield: 1.8 g (25% of theoretical) white product which changes to blue slowly in daylight. When exposed to UV light, it changes to dark blue within 15 seconds time. The product was confirmed by IR and elemental analyses. Additional product was obtained by adding 200 mL xylene to the dark viscous layer of the filtrate of step (e) after pouring off the top ether layer, boiling, then filtering through MgSO. After cooling to 50° C., 3.2 g (0.045 mole) ethylisocyanate was added. The product (containing both symmetrical and unsymmetrical compounds) was precipitated with heptane after ½ hour, filtered, and washed with additional heptane. Yield: 2.1 g crude white product which changes to blue slowly in daylight and dark blue within 30 seconds under a UV lamp.

EXAMPLE P

Color Response Broadening from Co-Crystallization

A solution composed of 1.2 g 2,4-hexadiyn-1,6-bis(ethylurea) (hereinafter referred to as 1KE) in 60 mL acetic acid was prepared; likewise a solution composed of 1.2 g 2,4-hexadiyn-1,6-bis(butylurea) (hereinafter referred to as 1KB) was also prepared. The solutions were mixed in the proportions shown in Table I and precipitated with an equal volume (about 10 mL) of petroleum ether (50°–110° C.), filtered and dried. The color responses of the co-crystalized composition were visually monitored. After 3 days at ambient conditions (about 25° C.) in the dark the co-crystallized compositions were assigned a relative reactivity value from 1 to 4.

TABLE I

| Visual Color Response and Relative Reactivity for Co-Crystallized 1KE and 1KB | | | | | |
|---|---|---|---|---|---|
| Soln 1KE | (mls) 1KB | Soln 1KE | (%) 1KB | Visual Color Response After 3 days | Relative Reactivity |
| 10.0 | 0.0 | 100 | 0 | light gray blue | 3 |
| 9.5 | 0.5 | 95 | 5 | light to med. blue | 1 (most reactive) |
| 9.0 | 1.0 | 90 | 10 | light blue to light med. blue | 2 |
| 5.0 | 5.0 | 50 | 50 | off-white | |
| 1.0 | 9.0 | 10 | 90 | off-white | |
| 0.5 | 9.5 | 5 | 95 | pale blue | 4 |
| 0.0 | 10.0 | 0 | 100 | yellow-orange | |

EXAMPLE Q

Characterization of Incremental Reflectivity Changes

An ink was formed by mixing 12.5 grams of 2,4-hexadiyn-1,6-bis(ethylurea) (1KE) with 36 ml of n-butanol and grinding this mixture in a ball mill for 16 hours. 10 grams of this suspension was mixed with 22.5 grams of a 12% (w/w) solution of Ethocell 45 dissolved in n-butanol. A portion of the ink was diluted so that the diluted ink had an acetylenic concentration that was only one half of the acetylenic concentration of the non-diluted ink.

A number of indicator labels were prepared by printing a rectangular image (0.3 cm×2.1 cm) on pressure sensitive white labels with the ink. A solid black bar (0.2 cm×2.1 cm) was printed on each side of the acetylenic urea bar at distance of 0.2 cm from the outer edge of the acetylenic urea bar. Thus, a white space 0.2 cm wide was between the acetylenic urea bar and the black bars. Thereafter, the labels were placed in controlled temperature baths (i.e. 60° C., 40° C., and 30° C.), and removed periodically in order to determine the reflectance of the indicator after exposure to a given temperature for a given period of time. Upon removal of the indicators from the temperature controlled compartments, each indicator was scanned with an Intermec 1401 scanning wand. The signal generated was forwarded through an amplifier (Signal Control Module T 22050, Scan-a-matic Corp.) and into a TECH LAB I computer. The signal was processed by averaging the reflectance values of the white (W) sections and black (B) bars and the reflectance values of the acetylenic urea bars (AC) as $$R = \frac{AC - B}{W - B}.$$

This value was used to determine the reflectance of the acetylenic urea compound relative to the white and black reference colors. These data are presented in Tables II, III, and IV.

TABLE II

| | Temperature 60° C. | |
|---|---|---|
| Time (Days) | Indicator 1 % Reflectance | Indicator 2* % Reflectance |
| 0 | 99 | 98 |
| 0.11 | 94 | — |
| 0.25 | 90 | — |
| 0.37 | 83 | 92 |
| 0.59 | 77 | 87 |
| 1.08 | 64 | 78 |

TABLE II-continued

Temperature 60° C.

| Time (Days) | Indicator 1<br>% Reflectance | Indicator 2*<br>% Reflectance |
|---|---|---|
| 1.97 | 39 | 59 |
| 2.91 | 25 | 44 |
| 3.68 | 17 | 33 |
| 4.41 | 12 | 27 |
| 4.71 |    | 25 |

*Indicator 2 had an acetylenic urea concentration equal to one half that of Indicator 1.

TABLE III

Temperature 40° C.

| Indicator 3* | | Indicator 4* | |
|---|---|---|---|
| Time (Days) | % Reflectance | Time (Days) | % Reflectance |
| 0 | 98 | .0 | 98 |
| 0.11 | 99 | 0.11 | — |
| 1.01 | 95 | 1.01 | — |
| 1.81 | 94 | 1.81 | 96 |
| 2.03 | 93 | 4.84 | 93 |
| 2.52 | 93 | 5.33 | 90 |
| 9.35 | 76 | 12.16 | 81 |
| 20.43 | 53 | 18.37 | 71 |
| 24.64 | 46 | 23.24 | 61 |
| a | 15 | 27.45 | 57 |
|   |    | b | 26 |

*Indicator 4 had an acetylenic urea concentration equal to that of Indicator 2, Indicator 3 had an acetylenic urea concentration equal to that of Indicator 1.
a - stored for 49 additional hours at 60° C.
b - stored for 49 additional hours at 60° C.

TABLE IV

Temperature 30° C.

| Time (Days) | Indicator 5*<br>% Reflectance | Indicator 6*<br>% Reflectance |
|---|---|---|
| 0 | 99 | 98 |
| 3.8 | 95 | 98 |
| 24.0 | 86 | 93 |
| 63.9 | 66 | 80 |

*Indicator 6 had a acetylenic urea concentration equal to that of Indicator 2, Indicator 5 had an acetylenic urea concentration equal to that of Indicator 1.

The data in Tables, II, III, and IV illustrate that percent reflectance is a function of time, temperature and concentration of indicating material, with higher temperatures, longer exposures and higher concentrations of indicating materials resulting in a more rapid decrease in reflectance. Using the data in Tables II and III, an activation energy of 29 kcal/mol was determined for 1KE. The activation energy was calculated from these data by determining the time necessary to reach a given reflectance value at two temperatures using a form of the Arrhenius equation.

EXAMPLE R

Color Characterization

1KE and 2,4-hexadiyn-1,6-bis(butylurea) (1KB) inks having a concentration equal to the non-diluted 1KE ink of Example Q were produced as in Example Q. 1 cm diameter dots of these inks were screen printed on Kimdura substrate. Thereafter, the dot indicators were placed on a Mettler hot stage for varying lengths of time at 110° C. and 90° C. The colors of the dot indicators exposed to these temperatures for varying lengths of time were correlated with the Munsell Color Code. The results appear in Tables V and VI.

TABLE V

Temperature 110° C.

| Time (min.) | 1KE<br>Munsell Color Code | | 1KB<br>Munsell Color Code | |
|---|---|---|---|---|
| 0 | 10PB | 8/2 | 2.5P | 9/2 |
| 6 | 10PB | 6/4 | 10PB | 4/8 |
| 11 | 10PB | 4/6 | 7.5PB | 4/8 |
| 24 | 2.5P | 3/4 | 5PB | 3/8 |
| 31 | 2.5P | 2.5/4 | 5PB | 3/8 |
| 42 | 2.5P | 2.5/2 | 5PB | 3/6 |
| 53 | 5P | 2.5/2 | 5PB | 3/6 |
| 64 | 10PB | 3/1 | 5PB | 3/6 |
| 100 | 5R | 2.5/1 | 5PB | 3/6 |
| 118 | 54R | 2.5/1 | 5PB | 3/4 |
| 139 | — | | 5PB | 3/4 |
| 203 | — | | 5PB | 3/4 |
| 251 |   |   | 5PB | 3/2 |

TABLE VI

Temperature 90° C.

| Time (min.) | 1KE<br>Munsell Color Code | | 1KB<br>Munsell Color Code | |
|---|---|---|---|---|
| 0 | 5PB | 8/1 | 2.5P | 9/2 |
| 6 | 5P | 7/4 | 2.5PB | 5/6 |
| 18 | 2.5P | 6/6 | 7.5PB | 4/6 |
| 38 | 5P | 5/6 | 7.5PB | 4/6 |
| 104 | 2.5P | 3/8 | 7/5PB | 3/6 |
| 133 | 2.5PB | 3/8 | 7.5PB | 3/4 |
| 170 | 2.5PB | 3/4 | 7.5PB | 3/4 |
| 192 | 2.5 | 2.5/4 | 7.5PB | 3/4 |
| 230 | 7.5PB | 2.5/4 | 7.5PB | 3/4 |

The results of Examples Q and R illustrate that 1KE and 1KB can be employed to monitor a wide variety of perishable products, or processes. For example, the data of Example Q demonstrate that 1KE can be employed to monitor a product with a shelf-life of about 1.5–3 years at 25° C. The results also demonstrate that by increasing the acetylenic urea concentration one can monitor periods of time of one year or shorter at room temperature. The results of Example R demonstrate that the color changes associated with the compounds tested could be used to verify that foodstuff cans have been properly sterilized by thermal treatment, as some cans for this purpose are subjected to temperatures in the 90° C.–100° C. range for 10–30 minutes for sterilization purposes.

ACETYLENIC COMPLEX EXAMPLES

The following examples and tables categorize the behavioral characteristics of various acetylenic complexes of the present invention.

Complexes were obtained by either vapor exposure to a halo-acid on a filter paper loaded with the conjugated acetylenic derivatves (presented as coded samples) or by direct contact with the concentrated acid with or without a Group II metal salt. The methods, testing, and results are given in the following examples. A key to the coding of the acetylenic deriviatives is presented first for ease of reference.

| CORRESPONDING PREPARATION EXAMPLES | Diacetylenic Derivatives KEY TO CODE | | | |
|---|---|---|---|---|
| | CODE | R-GROUP | SCHEME | STRUCTURE # |
| H | 1KM | $CH_3$ | 1 | 1 |
| A | 1KE | $C_2H_5$ | 1 | 1 |
| F | 1KPR | $C_3H_7$ | 1 | 1 |
| G | 1KIP | $(CH_3)_2CH$ | 1 | 1 |
| B | 1KB | $C_4H_9$ | 1 | 1 |
| C | 1KO | $C_8H_{17}$ | 1 | 1 |
| D | 1KDD | $C_{12}H_{25}$ | 1 | 1 |
| E | 1KOD | $C_{18}H_{37}$ | 1 | 1 |
| K | 1KP | $C_6H_5$ | 1 | 1 |
| I | 1KBCMU | $C_2H_5OOCCH_2$ | 1 | 1 |
| J | 1KBCMU | $C_4H_9OOCCH_2$ | 1 | 1 |
| L | STKM | $CH_3$ | 2 | 2 |
| L | STKE | $C_2H_5$ | 2 | 2 |
| L | STKDD | $C_{12}H_{25}$ | 2 | 2 |
| L,M,N | SHKM | $CH_3$ | 3 | 3 |
| N | SHKE | $C_2H_5$ | 3 | 3 |
| L,M,N | SHKDD | $C_{12}H_{25}$ | 3 | 3 |
| O | 4KE | $C_2H_5$ | 1 | 1; X = 4 |
| A | 1KH | $C_6H_{13}$ | 1 | 1 |

EXAMPLE 1

10 g of 1KE (Scheme 1 where R=ethyl) was dissolved in 100 ml HCl (36%) by heating to 65°–70° C. and immediately removed and allowed to cool; an evolution of gas occurred between 65°–70° C. during the heat-up. After cooling it was filtered, washed with xylene, and finally with petroleum ether (50°–110° C.) then air dried for ½ hour resulting in an off white product.

Testing and Results: A sample was set under a UV lamp for 2 minutes; no color change occurred. After adding a small amount of water to the sample and resetting it under a UV lamp, an immediate color change to blue resulted. Another sample was set in a vacuum oven for 16 hours. Checking a portion of the vacuum treated sample under a UV lamp resulted in no color change until water was added. Dissolution and recrystallization from acetic acid also restored activity. Contact with N,N,N',N'-tetramethylethylenediamine and glycerol also activated the compound even though these solvents do not dissolve the monmeric particles.

EXAMPLE 2

5 g of 1KE was added to 50 ml HBr (48%) and heated to 80° C. then immediately removed from the heat source (not all particles dissolved). After cooling and filtering, the product was washed with xylenes followed by heptane and air dried. The product was a pinkish-orange which changes to a bright orange after UV exposure.

Testing and Results: A portion was dried in a vacuum oven at room temperature for 4 hours. Under a UV lamp, a sample of the 4 hour vacuum treated sample changed to a bright orange. Addition of water caused the sample to transform and change to black blue.

EXAMPLE 3

0.5 g 1KE was treated in 5 ml HI (47%) by heating to 60° C. On cooling, the precipitated particles were a bright yellow. They were filtered, washed with xylenes, and then heptane.

Testing and Results: Under a UV lamp the yellow particles slowly became orange (5 minutes); treatment with water changes the particles to a brown color which is due to the effects of the HI. If the yellow particles are treated with water, they change to blue under UV.

EXAMPLE 4

0.5 g 1KE was dissolved in 3 ml HF (49%). The 1KE dissolved immediately. The product was precipitated with ethanol, filtered, washed with additional ethanol, and dried, resulting in a pure white product.

Testing and Results: A small quantity was set under a UV lamp; it immediately changed to blue indicating that the HF treatment was uneffective as compared to the H Cl, HBr, and HI treatments, possibly due to the hydrolytic effects of the ethanol, decomplexing the compound and restoring reactivity prematurely.

EXAMPLE 5

A small amount of material from Examples 1 to 4 was spread on filter paper substrates and exposed to UV light for 2 minutes. The results are listed in the table as follows.

TABLE 1

COMPARATIVE COLOR-RESPONSE OF THE HALO-DERIVATIVES OF 1KE AFTER 2 MINUTES OF UV EXPOSURE

| Derivative | Initial Color | COLOR RESPONSE After UV Exposure |
|---|---|---|
| F | white | medium blue |
| Cl | white | white |
| Br | pink-orange | bright orange |
| I | yellow | orange |

Results: All except the flouride derivative inactivated the 1KE in this experiment. However, the iodine derivative does eventually change slowly to brown due to its photoreactivity.

EXAMPLE 6

1 g (0.004 mole) 1KE, 40 ml HCl (36%), and 0.44 g (0.004 mole) $CaCl_2$ were heated to a boil and recrystallized at −26° C. overnight. After filtration, a wet sample was tested under a UV lamp; it changed from white to a bright red. After washing with ether and drying, it remained inactive when UV tested. Elemental analysis indicates 0.33% Ca and 22.04% Cl indicating a small amount of incorporated metal.

EXAMPLE 7

Repeated Example 6 except 0.81 g (0.004 mole) MgCl$_2$.6H$_2$O was used instead of the CaCl$_2$.

Results: In the wet state, it rapidly changes to orange then red (5 sec.) under a UV lamp. In the dry state it remained white under UV. Elemental analysis indicates 0.06% Mg and 22.15% Cl, again indicating the presence of a meager amount of the metal component.

EXAMPLE 8

Repeated Example 6 except 1.1 g (0.004 mole) SrCl$_2$ 6H$_2$O was substituted for the CaCl$_2$. Prior to recrystallization, the insoluble portion was separated.

Result: In the wet state, the color changed to red under UV (10 sec.); in the dry state, it remained white. Elemental analysis indicates 32.0% Sr and 27.18% Cl which may be due to unincorporated free SrCl$_2$.

Comparative results for Examples 6, 7 and 8 after 70 days:

The Ca and Mg derivatives were completely off-white whereas the Sr-derivative had some slight blue portions. Under a UV lamp they remained off-white. After treatment with water they readily changed to blue when exposed to UV light indicating their activatability even after such an extended period of being in an inactive form.

EXAMPLE 9

Di-urea compounds were spread on a filter paper substrate and exposed to HCl (36%) vapor. The HCl was contained in a one-gallon plastic jug with a narrow-mouthed opening. Each substrate was placed over the narrow-opening from 1 to 2 minutes and removed after a slight color changed was noted. Afterwards the color response, if any, was noted. The sample was left at room temperature ambient conditions up to 15 minutes to note if any additional color changed occurred. A fresh non-UV treated sample, which had been exposed to HCl vapor, was wetted and then exposed to UV light and its color change observed.

The di-ureas tested were tabulated and presented in the following 6 categories:

(1) Table 2: Inactivation of Active Di-Ureas by HCl (36% vapor). These compositions are completely inactive after HCl treatment; that is, UV treatment does not result in any color change; whereas non-HCl treatment does. Reactivaction occurs when water is added.

TABLE 2

| | INACTIVATION OF ACTIVE DI-UREAS BY HCL (36% VAPOR) | | |
|---|---|---|---|
| | COLOR RESPONSE AFTER | | |
| CODE | HCl then UV | HCl then UV then time lapse | HCl then H$_2$O then UV |
| 1KE | orange-yellow | orange-yellow (5 m) | dark blue (10 s) |
| 4KE | yellow | yellow (5 m) | blue (60 s) |

(2) Table 3: Activation of non-active Di-Ureas by HCl (36%, vapor). Prior to HCl treatment, no color-response occurs for these compositions under UV. But after HCl treatment followed by UV exposure, a color-response is observed. The addition of water followed by UV inactivates the color-responsivity.

TABLE 3

| | ACTIVATION OF NON-ACTIVE DI-UREAS BY HCl (36%, vapor) COLOR AFTER | | |
|---|---|---|---|
| CODE | HCl then UV | HCl then UV Then Time Lapse | HCl Then H$_2$O Then UV |
| 1KIP | Orange (60 s) | red | brown (60 s) |
| STKM | red (60 s) | blue (3 m) | brown (60 s) |

(3) Table 4: Non-Inactivation of Active Di-Ureas by HCl (36%, vapor). HCl treatment followed by UV exposure gives the same results as does UV exposure without any HCl treatment indicating that these compositions are not effected by the HCl vapor treatment.

TABLE 4

| | NON-INACTIVATION OF ACTIVE DI-UREAS BY HCl (36%, vapor) COLOR RESPONSE AFTER | | |
|---|---|---|---|
| CODE | HCl then UV | HCl then UV Then Time Lapse | HCl Then H$_2$O Then UV |
| 1KECMU | blue (30 s) | blue (5 m) | blue (30 s) |
| 1KDD | dark blue (1 m) | dark blue (5 m) | blue (1 m) |
| 1KOD | dark blue (1 m) | dark blue (5 m) | dark blue (1 m) |
| 1KP | light blue (5 m) | light blue (5 m) | light blue (5 m) |
| 1KO | dark metallic brown (60 s) | dark-metallic brown (5 m) | dark blue (20 s) |

(4) Table 5: Non-activation of Inactive DI-Ureas by HCl (36%, vapor). These compositions are non-responsive to UV light either before HCl treatment or afterwards.

TABLE 5

| | NON-ACTIVATION OF INACTIVE DI-UREAS BY HCl (36%, vapor) | | |
|---|---|---|---|
| | COLOR RESPONSE AFTER | | |
| CODE | HCl then UV | HCl then UV Then Time Lapse | HCl Then H$_2$O Then UV |
| 1KM | yellow (1 m) | yellow (5 m) | yellow (1 m) |
| SHKM | maroon (1 m) | maroon (5 m) | brownish (1 m) |

(5) Table 6: Spontaneous Change from Orange to Red by Moisture or water after HCl (36% vapor) followed by UV treatment of Active Di-Ureas. A color change to orange is observed after HCl followed by UV treatment; if water is added a spontaneous color change to red occurs. At room temperature the orange color changes to red in less than 15 minutes. Addition of water prior to UV results in normal color development after UV treatment.

TABLE 6

SPONTANEOUS CHANGE FROM ORANGE TO RED BY MOISTURE OR WATER AFTER HCl (36%, VAPOR) TREATMENT FOLLOWED BY UV EXPOSURE OF ACTIVE DI-UREAS
COLOR RESPONSE AFTER

| CODE | HCl then UV | HCl then UV Then Time Lapse | HCl then UV then $H_2O$ | HCl then $H_2O$ then UV |
|---|---|---|---|---|
| 1KB | orange (30 s) | red (<5 m) | red | dark blue (30 s) |
| 1KPR | orange (30 s) | red (<5 m) | red | green-blue (30 s) |
| 1KBCMU | orange (30 s) | | red | dark blue (60 s) |

(6) Table 7: Spontaneous Change from Red to Blue by Moisture or Water after HCl (36% vapor) followed by UV treatment of Active Di-Ureas. Same as Table 6 except a red to blue color change occurs.

TABLE 7

SPONTANEOUS CHANGE FROM RED TO BLUE BY MOISTURE OR WATER AFTER HCl (36%, VAPOR) TREATMENT FOLLOWED BY UV EXPOSURE OF ACTIVE DI-UREAS
COLOR RESPONSE AFTER

| CODE | HCl then UV | HCl then UV Then Time Lapse | HCl then UV the $H_2O$ | HCl then $H_2O$ then UV |
|---|---|---|---|---|
| STKE | bright red (60 s) | med. blue (5 m) | dark blue | dark blue (60 s) |
| STKDD | bright red (60 s) | dark blue (1 m) | dark blue | brown-blue, (60 s) |
| SHKDD | bright red (60 s) | blue-purple (1 m) | blue-purple | blue-purple (60 s) |

SHKDD requires about 2 m HCl vapor contact.

EXAMPLE 10

Di-ureas were heated in hydrochloric acid to approximately 75° C. at the rate of 0.1 g/ml HCl (36%) then cooled, filtered, washed with xylenes followed by either heptane or petroleum ether (50°–110° C.); only the 1KM solubilized completely, the remainder were either partially soluble or totally insoluble in the media. The treatments and results are in the following tables with headings and descriptions as shown below:

(1) Table 8: Change In Color Response by HCl (36%, liquid) for Active Di-Ureas Not Effected by HCl (36%, vapor)

The di-ureas shown here are the same ones which appeared in Table 4 except for 1 KDD which did not result in any change in color-responsiveness after HCl vapor treatment. Table 8 indicates a change in color response not noted in Table 4.

TABLE 8

CHANGE IN COLOR RESPONSE BY HCl (36%, LIQUID) TREATMENT FOR ACTIVE DI-UREAS NOT EFFECTED BY HCl (36%, VAPOR)
COLOR RESPONSE AFTER

| CODE | HCl | HCl then UV | HCl then UV then $H_2O$ | HCl then $H_2O$ then UV |
|---|---|---|---|---|
| 1KECMU | orange | bright orange | dark blue | dark blue |
| 1KDD | red-orange | red-orange | blue-purple | med. blue (30 s) |
| 1KOD | brown-orange | orange | red-purple | med. blue (30 s) |
| 1KP | tan | bright red | | blue (30 s) |

(2) Table 9: Inactivation of Active Di-ureas by HCl (36%, liquid)
Of all the samples tested in both HCl and HBr, only the samples shown here (1KE and 4KE) become totally inactive after HCl (36%, vapor and liquid) treatment. These HCl treated samples do not change color under a UV lamp until they are reactivated by water.

TABLE 9

INACTIVATION OF ACTIVE DI-UREAS BY HCl (36%, LIQUID) COLOR RESPONSE AFTER

| CODE | HCl | HCl then UV | HCl then UV then $H_2O$ | HCl then $H_2O$ then Uv |
|---|---|---|---|---|
| 1KE | off-white | off-white | off-white | med. blue (30 s) |
| 4KE | off-white | off-white | off-white | med. blue (30 s) |

(3) Table 10: Activation of Non-Active Di-Ureas by HCl (36%, liquid)
These di-ureas do not change color; that is, they are inactive, prior to HCl treatment.

TABLE 10

ACTIVATION OF NON-ACTIVE DI-UREAS BY HCl (36%, LIQUID) COLOR RESPONSE AFTER

| CODE | HCl | HCl then UV | HCl then UV then $H_2O$ | HCl then $H_2O$ then UV |
|---|---|---|---|---|
| 1KIP | white | red-orange | med. red | orange then red |
| STKM | lt. red-purple | red-maroon | med. blue | reddish-tan |
| SHKM | pink | red | dark blue | light pink |

Without HCl treatment, all of the above remain white (inactive) indefinitely.
(4) Table II: Activity Increase by HCl (36%, liquid)
A dramatic change in color-responsiveness was observed for 1KO after HCl tratment; it changes to blue more rapidly.

TABLE 11

ACTIVITY INCREASE BY HCl (36%, LIQUID) COLOR RESPONSE AFTER

| CODE | HCl | HCl then UV | HCl then UV then H₂O | HCl then H₂O then UV |
|------|-----|-------------|----------------------|----------------------|
| 1KO  | off-white | dark-blue (30 s) | dark blue | med. blue (30 s) |

(5) Table 12: Spontaneous Change from Orange to Blue or Red-Purple by Moisture or Water after HCl (36%, liquid) followed by UV treatment of Active Di-ureas.

Some di-ureas which normally change to blue either thermally or under a UV lamp become orange after HCl treatment followed by UV light. Contact with water abruptly changes the color from orange to blue. If water is added after the HCl treatment, a blue color occurs during UV treatment.

TABLE 12

SPONTANEOUS CHANGE FROM ORANGE TO BLUE OR RED-PURPLE BY MOISTURE OR WATER AFTER HCl (36%, LIQUID) FOLLOWED BY UV TREATMENT OF ACTIVE DI-UREAS COLOR RESPONSE AFTER

| CODE | HCl | HCl the UV | HCl then UV then H₂O | HCl then H₂O then UV |
|------|-----|------------|----------------------|----------------------|
| 1KDD | med. red-orange | dark red-orange | med. blue-purple | med. blue |
| 1KOD | brown-orange | orange | red-purple | med. blue |
| 1KB | med. orange | bright-orange | red-purple | med. blue |
| 1KPR | off-white | orange | red-purple | lt. green-blue |
| 1KBCMU | orange | dark orange | blue | blue |

(6) Table 13: Spontaneous Change from Red to Blue by Moisture or Water after HCl (36%, liquid) followed by UV Treatment of Active Di-Ureas Same as Table 12 except a red to blue color change occurs.

NOTE: 1KM was not activatable by either HCl (36%, vapor) nor HCl (36%, liquid) The 1KECMU was treated cold with HCl avoiding solubilization and hydrolysis.

The above also undergo a spontaneous color change after UV exposure followed by water treatment.

TABLE 13

SPONTANEOUS CHANGE FROM RED TO BLUE BY MOISTURE OR WATER AFTER HCl (36%, LIQUID) FOLLOWED BY UV TREATMENT OF ACTIVE DI-UREA COLOR RESPONSE AFTER

| CODE | HCl | HCl then UV | HCl then UV then H₂O | HCl then H₂O then UV |
|------|-----|-------------|----------------------|----------------------|
| STKE | med. pink | bright red | med. to dark blue | med. to dark blue |
| SHKE | pink | red | med. to dark blue | med. to dark blue |
| STKDD | pink | bright red | med. blue | light blue |
| SHKDD | pink | red-purple | blue-purple | red-purple |
| 1KP | tan | bright red | | blue |

EXAMPLE 11

Same as Example 10 except HBr (48%, liquid) was used; none of the di-ureas tested were soluble in the HBr media. The treatment and results are in the following tables with headings and descriptions as shown below;

(1) Table 14: Activation of Non-Active Di-ureas by HBr (48%, liquid)

These are the same di-ureas as shown in Table 10 except for STKM, which seems to deactivate after water treatment.

TABLE 14

ACTIVATION OF NON-ACTIVE DI-UREAS BY HBr (48%, LIQUID) COLOR RESPONSE AFTER

| CODE | HBr | HBr then UV | HBr then UV then H₂O | HBr then H₂O then UV |
|------|-----|-------------|----------------------|----------------------|
| 1KIP | light yellow | dark yellow | red | light red |
| SHKM | light pink | red | blue | light pink |

(2) Tables 15 and 16: Deactivation of an Active Di-urea after HBr (48%, liquid) Treatment 1KP, the only entry in Table 15, normally changes to blue slowly under a UV lamp without any acid treatment. However, after HBr treatment, no color change occurs after UV treatment or water treatment followed by UV.

TABLE 15

DEACTIVATION OF AN ACTIVE DI-UREA AFTER HBr (48%, LIQUID) TREATMENT COLOR RESPONSE AFTER

| CODE | HBr | HBr then UV | HBr then UV then H₂O | HBr then H₂O then UV |
|------|-----|-------------|----------------------|----------------------|
| 1KP | lt. red-purple | lt. red-purple | lt. red-purple | lt. red-purple |

TABLE 16

FADING (DEACTIVATION) OF NON-ACTIVE DI-UREAS DUE TO MOISTURE OR WATER AFTER HBr (48%, LIQUID) TREATMENT FOLLOWED BY UV ACTIVATION COLOR RESPONSE AFTER

| CODE | HBr | HBr then UV | HBr then UV then H₂O | HBr then H₂O then UV |
|------|-----|-------------|----------------------|----------------------|
| 1KM | pink | red | orange-tan | yellow |
| STKM | lt. red-purple | red | lt. reddish-tan | lt. reddish brown |

(3) Table 17: Spontaneous Change from Orange to Blue by Moisture or Water after HBr (48%, liquid) Treatment followed by UV Exposure of Active Di-Ureas Without HBr treatment, these compositions (1KE and the active phase of 1KB) change to blue either thermally or with UV light. After HBr treatment, they change from orange to blue after Uv exposure followed by water treatment. Water contact after HBr treatment followed by UV exposure gives the normal blue color for the 1KE but does not for the 1KB; it changes to the brownish-red.

TABLE 17
SPONTANEOUS CHANGE FROM ORANGE TO BLUE BY MOISTURE OR WATER AFTER HBr (48%, LIQUID) TREATMENT FOLLOWED BY UV EXPOSURE OF ACTIVE DI-UREAS

| | COLOR RESPONSE AFTER | | | |
|---|---|---|---|---|
| CODE | HBr | HBr then UV | HBr then UV then H$_2$O | HBr then H$_2$O then UV |
| 1KE | orange | bright orange | black-blue | dark blue |
| 1KB | med. orange | dark orange | blue | brownish-red |

(4) Table 18: Spontaneous Change from Red to Blue by Moisture or Water after HBr (48%, liquid) Treatment followed by UV Exposure for some Active Di-ureas Similar to Table 16 except these compositions (STKE and SHKE) change from red to blue after HBr treatment followed by UV exposure followed by water contact. Contact with water after HBr treatment followed by UV exposure gives the normal blue color-response.

TABLE 18
SPONTANEOUS CHANGE FROM RED TO BLUE BY MOISTURE OR WATER AFTER HBr (48%, LIQUID) TREATMENT FOLLOWED BY UV EXPOSURE FOR SOME ACTIVE DI-UREAS

| | COLOR RESPONSE AFTER | | | |
|---|---|---|---|---|
| CODE | HBr then UV | HBr then UV then H$_2$O | HBr then UV then H$_2$O | HBr then H$_2$O then UV |
| STKE | med. red-purple | red | med. blue | med. blue |
| SHKE | rose-pink | red | dark blue | light blue |

(5) Table 19: Spontaneous Change from Red to Blue by Moisture or Water after HBr (48%, liquid) Treatment followed by UV Exposure of an Inactive Di-urea Same as Table 18 except that the one di-urea listed (SHKM) is inactive when not treated with a halo-acid. If water is added prior to UV exposure, it is virtually inactive; the light pink color is essentially the color of the starting HBr treated sample.

TABLE 19
SPONTANEOUS CHANGE FROM RED TO BLUE BY MOISTURE OR WATER AFTER HBr (48%, LIQUID) TREATMENT FOLLOWED BY UV EXPOSURE OF AN INACTIVE DI-UREA

| | COLOR RESPONSE AFTER | | | |
|---|---|---|---|---|
| CODE | HBr | HBr then UV | HBr then UV then H$_2$O | HBr then H$_2$O then UV |
| SHKM | light pink | red | dark blue | light pink |

(6) Table 20: Spontaneous Change rom Orange to Red by Moisture or Water after HBr (48%, liquid) Treatment followed by UV Exposure of some Active Di-ureas Without HBr treatment (also HCl), these compositions change to blue either thermally or under UV lamp. In contrast, with HBr treatment, they change to orange under a UV lamp. The samples spontaneously change from orange to red when contacted with water. If contact with water is made after HBr treatment and prior to UV exposure, UV treatment gives the color effects shown in the table.

TABLE 20
SPONTANEOUS CHANGE FROM ORANGE TO RED BY MOISTURE OR WATER AFTER HBr (48%, LIQUID) TREATMENT FOLLOWED BY UV EXPOSURE OF ACTIVE DI-UREAS

| | COLOR RESPONSE AFTER | | | |
|---|---|---|---|---|
| CODE | HBr | HBr then UV | HBr then UV then H$_2$O | HBr then H$_2$O then UV |
| 1KPR | tannish-orange | bright orange | brownish-red | brownish-red |
| 1KO | light tan | dark orange | brownish-red | med. blue |
| 1KDD | light orange | bright orange | med. red | lt. red-orange |
| 1KBCMU | med. orange | dark orange | dark brown-red | dark blue |

EXAMPLE 12

The HCl (36%, liquid) treated samples were left in capped glass vials which do not provide a total seal without UV-irradiation at room-temperature ambient conditions; after 70 days, the color development was observed. The initial and final colors (70 days) are shown in Table 21. Also shown is the Cl elemental analysis.

TABLE 21
COLOR RESPONSE AFTER 70 DAYS BOR HCl TREATED DI-UREAS SEALED IN VIALS

| | COLOR RESPONSE | | ELEMENTAL Cl (%) | |
|---|---|---|---|---|
| CODE | Initial | Final (70 days) | Calc. | Found |
| 1KM | — | — | 24.02 | — |
| 1KB | off-white | off-white | 21.94 | 22.30 |
| 1KPR | off-white | black-blue | 20.19 | 4.00 |
| 1KIP | white | med. red-purple | 20.19 | — |
| 1KB | med. orange | black-blue | 18.69 | — |
| 1KO | off-white | dark blue | 14.43 | 0.20 |
| 1KDD | med. red-orange | med. blue | 11.74 | — |
| 1KOD | brown-orange | med. blue | 9.18 | 1.08 |
| 1KP | tan | — | 16.91 | — |
| 1KECMU | | med. red | 16.14 | 0.14 |
| 1KBCMU | orange | black-blue | 14.32 | 0.20 |
| STKM | lt. red-purple | maroon-red | 19.10 | 5.16 |
| STKE | med. pink | dark blue | 17.49 | 0.50 |
| STKDD | pink | med. gray-blue | 10.43 | 1.87 |
| SHKM | pink | med. brown-red | 15.85 | — |
| SHKE | pink | black-blue | 14.91 | — |
| SHKDD | pink | med. blue-purple | 9.38 | <0.10 |

Those compositions which changed to either a dark blue (1KO and STKE) and especially those which changed to a black blue (1KB, 1KPR, 1KBCMU, and SHKE) shown in Table 21 may have an enhanced color-response as compared to non-HCl treated samples. Table II also indicates this possibility for the 1KO.

EXAMPLE 13

Same as Example 12 except HBr (48%, liquid) rather than HCl (36%, liquid) was used and is depicted in Table 22.

Within the 70 day period, all of the tested HCl treated samples changed to a shade of blue except: (1) those which are inactive prior to HCl treatment (1KIP, STKM, and SHKM); (2) Surprisingly, 1KECMU was not blue but rather a bright red with scattered blue specs; (3) also 1KE remained inactive and was off-white except for a vacuum treated sample which had a sight blue coloration.

TABLE 22
COLOR RESPONSE AFTER 70 DAYS FOR HBr TREATED DI-UREAS SEALED IN VIALS

| CODE | COLOR RESPONSE Initial | COLOR RESPONSE Final (70 days) | ELEMENTAL; Br (%) Calc. | ELEMENTAL; Br (%) Found |
|---|---|---|---|---|
| 1KM | pink | med. rose-red | 41.61 | 41.23 |
| 1KE | orange | bright orange | 38.78 | 38.75 |
| 1KPR | tan-orange | lt. yellow | 36.31 | 39.75 |
| 1KIP | lt. yellow | med. yellow | 36.31 | 36.70 |
| 1KB | med. orange | med. orange | 34.13 | 28.37 |
| 1KO | light tan | med. yellow | 27.53 | 31.16 |
| 1KDD | lt. orange | med. red-brown | 23.07 | 22.92 |
| 1KOD | brown-orange | red-orange | 18.56 | 18.08 |
| 1KP | lt. red-purple | lt. red-gray | 31.45 | 19.36 |
| 1KECMU | | light tan | 30.26 | 4.37 |
| 1KBCMU | med. orange | brown-orange | 27.35 | 34.10 |
| STKM | lt. red-purple | med. red-purple | 34.73 | 34.53 |
| STKE | med. red-purple | med. red-purple | 32.33 | 31.73 |
| STKDD | pink-tan | lt. rose-pink | 20.79 | 15.70 |
| SHKM | light pink | dark red-purple | 29.80 | — |
| SHKE | rose-pink | med. red-purple | 28.32 | — |
| SHKDD | pink | med. red-purple | 18.92 | 13.70 |

None of the HBr treated compositions changed to blue within the 70 day period. They changed basically to either yellow, red, or orange.

MOISTURE SENSITIVE SYSTEMS

The halo-bromide urea derivatives provide a stable system for moisture detection. They are preferable to the halo-clorides in that they tend to maintain their complexed state for relatively long periods of time.

The 1KE/HBr derivative was tested for its moisture sensitivity, which is visibly recognizable by its orange to blue color response. The complex was prepared by contacting the 1KE with HBr, followed by filtration, washing and drying. It was kept in an ordinary jar for at least two years at ambient room temperature. The only notable change during this time was a moderate intensification of its orange color. To obtain a bright orange color, the test samples were spread on a filter paper substrate and treated for 5 to 10 seconds under a UV lamp.

The 1KE/HBr was coated on 1 cm² filter paper substrates and treated with 5 seconds UV exposure. If a barrier film was used, 2 sides were initially sealed followed by 15 to 30 minute vacuum treatment prior to sealing the 4th side. Humidity baths were prepared using various reagents to obtain a broad range of relative humidities. The samples were set above the bath levels and the humidity chambers sealed to allow for equilibration. The results are as follows:

A. CONTROLS
TABLE 23
COLOR RESPONSE OF 1KE/HBr ON FILTER PAPER SUBSTRATES IN VARIOUS RELATIVE HUMIDITY ENVIRONMENTS

| Reagent | Relative Humidity % | Time For Orange→Blue Color Transition |
|---|---|---|
| CaCl$_2$.6H$_2$O | 32.3 (20° C.) | orange (40 hours) |
| K$_2$CO$_3$.2H$_2$O | 43 (24.5° C.) | brown (24 hrs); blue (40 hrs) |
| NaHSO$_4$.H$_2$O | 52 (20° C.) | 55 to 65 minutes |
| Ca(NO$_3$)$_2$.6H$_2$O | 56 (18.5° C.) | 45 to 60 minutes |
| NaBr.2H$_2$O | 58 (20° C.) | 45 to 60 minutes |
| NaNO$_3$ | 66 (20° C.) | 15 to 20 minutes |
| KBr | 84 (20° C.) | 5 to 10 minutes |
| H$_2$O | 100 | spontaneous |

B. FILM BARRIERS (1) Vinylidene fluoride chlorotrifluoroethylene, Aclar ® (2 mil); orange-brown after 27 days at 100° Rel. Humidity (R.H.)

(2) Polyethylene (1.5 mil); ½ blue at 66% R.H. and completely blue at 86% R.H. after 50 hours.

(3) Polyester (4.5 mil); 3/4 blue at 66% R.H. and completely blue at 86% R.H. after 72 hours.

(4) All of the above films with indicators left in a 32.3% R.H. environment changed to orange-brown but not blue after 14 days.

CONCLUSIONS (a) The indicator undergoes an orange to blue or orange to orange-brown to blue transition easily when the relative humidity is above about 50%; approx. 1 hour at 52%, 5 to 10 minutes at 84%, and spontaneously at 100%.

(b) The color transition is extended when a film barrier such as polyethylene or polyester is used.

(c) When vinylidene fluoride-chlorotrifluoroethylene (Aclar ® 2 mil) was used, no end point was observed after 14 days, indicating it to be a good barrier material.

(d) At relative humidities below about 50%, activity is reduced, however, at relative humidities of about 30 to 35%, some darkening to a brown color was noted when the material was spread out on a paper substrate.

IRREVERSIBILITY OF DEVELOPED COLOR (1) A blue colored sample obtained by exposure to 66% relative humidity for 5½ hours was set in a Mettler hot stage starting @50° C. Every 5 minutes, the temperature was increased by 10° C. until reaching 130° C.
Results: The sample became a dark blue (2) Another sample from the 66% R.H. bath was set in a vacuum overnight @ room temperature.
Results: It changed to a dark blue-purple (3) Another sample from the 66% R.H. bath was set on a Mettler hot stage @70° C. for 16 hours.
Results: The sample intensified in blue color

CONCLUSION

The compositions' color-response activity is irreversible, that is the blue does not revert back to orange either when heated or treated in a vacuum oven.

We claim:

1. An acetylenic complex comprising at least one complexing agent and at least one acetylenic compound of the general formula:

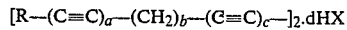

$$[R-(C{\equiv}C)_a-(CH_2)_b-(C{\equiv}C)_c-]_2 \cdot dHX$$

Wherein:
a is 1 or 2, b is a whole number from 0 to 5, c is 0 or 1, and d is a whole number from 0 to 2; with the proviso that when a is 1, b and c are 0; and R is —(CH$_2$)$_n$—NHC(O)NHR'
wherein:
(1) n is an integer of about 1 to 10; and
(2) R' is selected from the group consisting of:
(a) hydrogen;
(b) cycloalkyl;
(c) alkenyl;
(d) cycloalkenyl;
(e) alkyl;
(f) phenyl;
(g) alkoxyl;

(h) alkoxylalkyl;
(i) alkoxylcarbonylalkyl;
and HX is an effective complexing acid; said acetylenic complex capable of demonstrating reactivity by undergoing one or more color changes upon exposure to stimuli.

2. A complex in accordance with claim 1 wherein said acetylenic compound is of the structure:

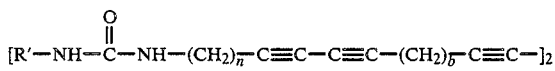

wherein R' is an organic moiety selected from the group consisting of a cycloalkyl moiety of about 3–7 carbon atoms, an alkenyl moiety of about 3–18 carbon atoms, a cycloalkenyl moiety of about 3–7 carbon atoms, an alkoxy moiety of about 2–18 carbon atoms, a linear or branched alkyl moiety of about 1 to 18 carbon atoms, and an alkoxycarbonylmethylene moiety of about 3–14 carbon atoms; n is an integer of 1 to 4 and x is an integer of about 1 to 6.

3. A complex in accordance with claim 1 wherein said acetylenic compound is of the structure:

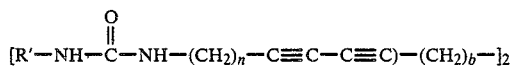

wherein R' is an organic moiety selected from the group consisting of a cycloalkyl moiety of about 3–7 carbon atoms, an alkenyl moiety of about 3–18 carbon atoms, a cycloalkenyl moiety of about 3–7 carbon atoms, an alkoxy moiety of about 2–18 carbon atoms, a linear or branched alkyl moiety of about 1 to 18 carbon atoms, and an alkoxycarbonylmethylene moiety of about 3–14 carbon atoms; n is an integer of 1 to 5; and x is an integer of 1 to 6.

4. A complex in accordance with claim 3 wherein R' is a linear or branched alkyl moiety of about 1–18 carbon atoms, or an alkoxycarbonylmethylene moiety of about 3–14 carbon atoms.

5. A complex in accordance with claim 1 wherein said acetylenic compound is of the structure:

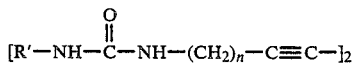

wherein R' is an organic moiety selected from the group consisting of a cycloalkyl moiety of 3–7 carbon atoms, an alkoxy moiety of about 3–7 carbon atoms, an alkenyl moiety of 3–18 carbon atoms, a cycloalkenyl moiety of about 3–7 carbon atoms, an alkoxy moiety of about 2–18 carbon atoms, a linear or branched alkyl moiety of about 1 to 18 carbon atoms, and an alkoxycarbonylmethylene moiety of 3–14 carbon atoms; and n is an integer of about 1 to 5.

6. A complex in accordance with claim 5 wherein R' is a linear alkyl moiety of about 1–18 carbon atoms.

7. A complex in accordance with claim 5 wherein R' is a linear alkyl moiety of about 2–10 carbon atoms and said complexing acid is selected from the group consisting of HBr and HCl.

8. A complex in accordance with claim 7 wherein R' is a linear alkyl moiety of about 2–4 carbon atoms and said complexing acid is HBr.

9. A complex in accordance with claim 8 wherein R' is ethyl.

10. A complex in accordance with claim 5 wherein R' is a linear or branched alkyl moiety of about 1–18 carbon atoms, or an alkoxycarbonylmethylene moiety of about 3–14 carbon atoms.

11. A complex in accordance with claim 10 wherein said complexing acid is selected from the group consisting of HI, HF, HBr, and HCl.

12. A complex in accordance with claim 11 wherein said complexing acid is HBr.

13. A compound in accordance with claim 12 wherein R' is butyl.

14. A complex in accordance with claim 11 wherein said complexing acid is HCl.

15. A complex in accordance with claim 14 wherein R' is ethyl.

16. An environmental exposure indicating device comprising a substrate having deposited thereon a complex in accordance with claim 1; said complex on said substrate capable of undergoing one or more color changes upon exposure to environmental stimuli to indicate changes in environmental conditions.

17. An environmental exposure indicating device in accordance with claim 16 capable of undergoing one or more color changes upon exposure to moisture.

18. A method of controlling the reactivity of acetylenic compounds of the general formula:

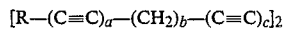

Wherein:
a is 1 or 2, b is a whole number from 0 to 5, c is 0 or 1; with the proviso that when a is 1, b and c are 0; and R is —(CH$_2$)$_n$—NHC(O)NHR'

Wherein:
(1) n is an integer of about 1 to 10; and
(2) R' is selected from the group consisting of:
  (a) hydrogen;
  (b) cycloalkyl;
  (c) alkenyl;
  (d) cycloalkenyl;
  (e) alkyl;
  (f) phenyl;
  (g) alkoxy;
  (h) alkoxylalkyl; and
  (i) alkoxylcarbonylalkyl;
said method comprising the step of contacting the compound with an effective complexing acid for a time sufficient to produce an acetylenic complex having a reactivity to environmental stimuli which differs from the reactivity of said acetylenic compound to said stimuli.

19. A method in accordance with claim 18 wherein the complexing acid is selected from the group consisting of hydro-halo acids.

20. A method in accordance with claim 19 wherein the reactivity of said acetylenic complex to environmental stimuli is greater than that demonstrated by the acetylenic compound in the absence of complexation.

* * * * *